(12) United States Patent
Karnes et al.

(10) Patent No.: US 8,797,517 B2
(45) Date of Patent: Aug. 5, 2014

(54) PVT ANALYSIS OF PRESSURIZED FLUIDS

(75) Inventors: Karl Karnes, Spring, TX (US); Lee Williams, Magnolia, TX (US)

(73) Assignee: SGS North America Inc., Rutherford, NJ (US)

( * ) Notice: Subject to any disclaimer, the term of this patent is extended or adjusted under 35 U.S.C. 154(b) by 125 days.

(21) Appl. No.: 13/387,545

(22) PCT Filed: Aug. 31, 2009

(86) PCT No.: PCT/US2009/055556
§ 371 (c)(1),
(2), (4) Date: Jan. 27, 2012

(87) PCT Pub. No.: WO2011/014202
PCT Pub. Date: Feb. 3, 2011

(65) Prior Publication Data
US 2012/0127466 A1 May 24, 2012

Related U.S. Application Data

(60) Provisional application No. 61/229,961, filed on Jul. 30, 2009.

(51) Int. Cl.
*G01J 3/42* (2006.01)
*G01N 25/00* (2006.01)

(52) U.S. Cl.
USPC .......................................................... 356/72

(58) Field of Classification Search
USPC .................................... 356/72–73, 300–334
See application file for complete search history.

(56) References Cited

U.S. PATENT DOCUMENTS

| | | | | |
|---|---|---|---|---|
| 3,789,890 A | * | 2/1974 | Riedel et al. | 141/144 |
| 4,890,482 A | * | 1/1990 | Maini | 73/54.14 |
| 5,383,352 A | | 1/1995 | Krawetz et al. | |
| 5,383,353 A | | 1/1995 | Marrelli et al. | |
| 5,417,106 A | * | 5/1995 | Grudzien et al. | 73/54.14 |

(Continued)

FOREIGN PATENT DOCUMENTS

| | | |
|---|---|---|
| CN | 1135793 A | 11/1996 |
| EP | 598644 A1 | 5/1994 |
| FR | 2666415 A | 3/1992 |
| RU | 2302631 C2 | 7/2007 |
| SU | 1469313 A1 | 3/1989 |

OTHER PUBLICATIONS

Ryu, Chang Yong, "Notification of Transmittal of the International Search Report and the Written Opinion of the International Searching Authority, of the Declaration", Int. Appl. No. PCT/US2009/055556, issued on Aug. 27, 2010 (13 pages).

(Continued)

*Primary Examiner* — Gregory J Toatley
*Assistant Examiner* — Dominic J Bologna
(74) *Attorney, Agent, or Firm* — Fish & Richardson P.C.

(57) ABSTRACT

Methods and systems for performing pressure-volume-temperature testing on fluids include: a portable environmental control chamber 14, a first pressure vessel 12A disposed inside the portable environmental control chamber, a second pressure vessel 12B disposed inside the portable environmental control chamber, the second pressure vessel in hydraulic communication with the first pressure vessel, a viscometer 18 configured to measure the viscosity of fluids flowing between the first pressure vessel and the second pressure vessel, and an optics system 22 configured to measure optical properties of fluids flowing between the first pressure vessel and the second pressure vessel.

29 Claims, 21 Drawing Sheets

(56) References Cited

U.S. PATENT DOCUMENTS

| | | | |
|---|---|---|---|
| 5,517,427 A * | 5/1996 | Joyce | 702/50 |
| 5,734,093 A * | 3/1998 | Miller, Jr. | 73/30.03 |
| 5,747,674 A | 5/1998 | Moracchini et al. | |
| 6,072,576 A * | 6/2000 | McDonald et al. | 356/300 |
| 6,455,850 B1 * | 9/2002 | Coates et al. | 250/338.1 |
| 6,755,079 B1 * | 6/2004 | Proett et al. | 73/152.18 |
| 7,467,540 B2 | 12/2008 | Kriel | |
| 2006/0070426 A1 | 4/2006 | Pelletier | |
| 2007/0089483 A1 | 4/2007 | Kriel | |
| 2011/0061935 A1 * | 3/2011 | Mullins et al. | 175/50 |
| 2012/0011919 A1 | 1/2012 | Azcarate et al. | |
| 2012/0272715 A1 | 11/2012 | Kriel et al. | |

OTHER PUBLICATIONS

Official Action for Kazakhstan Application No. 2012/1520.1, dated Apr. 25, 2013, 4 pages.

Decision on Grant issued in Russian Application No. 2012107525 on Jul. 4, 2013, 17 pages.

Office Action issued in Chinese Application No. 200980161796.6 on Sep. 22, 2013, 19 pages.

Decision on Grant issued in Kazakhstan Application No. 2012/1520.01 on Sep. 16, 2013, 10 pages.

* cited by examiner

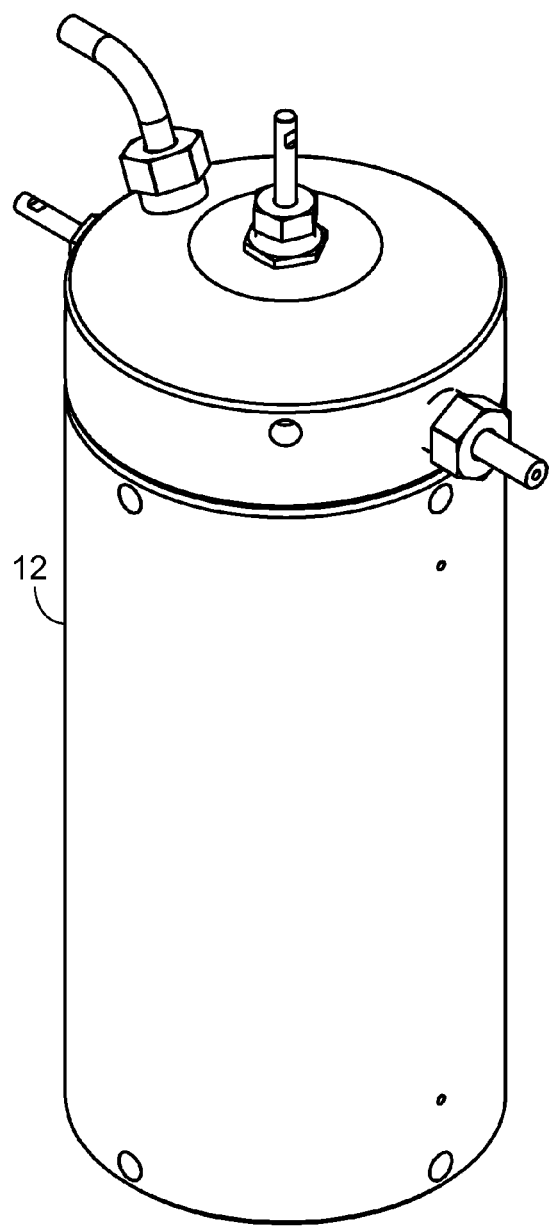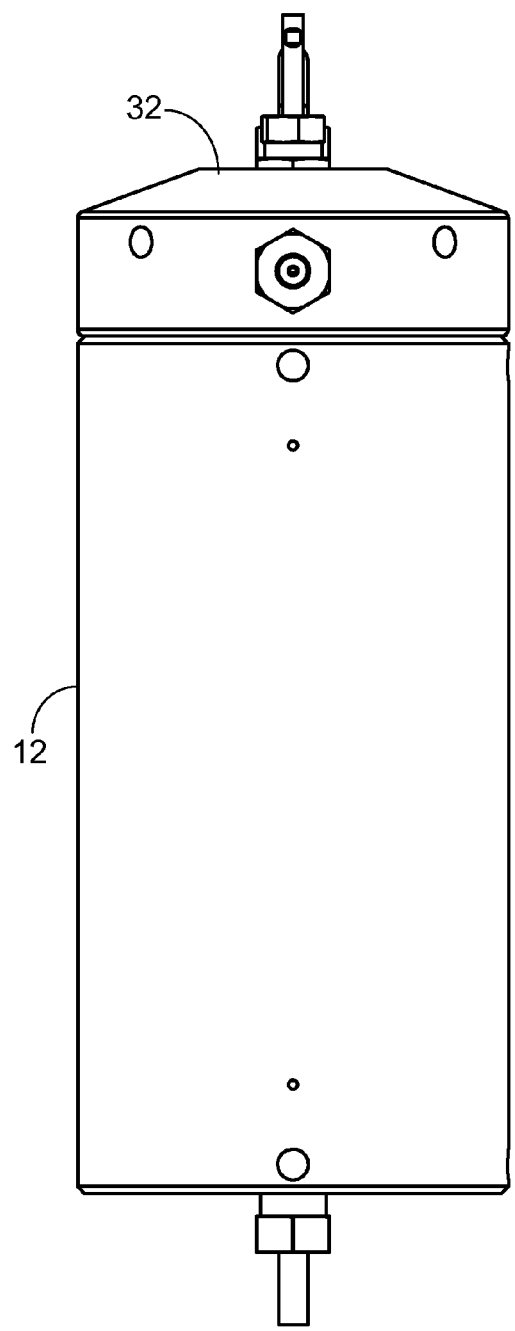
FIG. 2A                    FIG. 2B

Schematic Representation of Differential Liberation Experiment

Schematic Representation of Multi-Stage Separator Test Experiment

Schematic Representation of Constant Volume Depletion Experiment

PVT ANALYSIS OF PRESSURIZED FLUIDS

REFERENCE TO RELATED APPLICATIONS

The present application claims the benefit of priority to U.S. Patent Application No. 61/229,961 filed Jul. 30, 2009, the entire contents of which are incorporated herein.

TECHNICAL FIELD

This invention relates to portable analysis systems and methods.

BACKGROUND

Various pressure-volume-temperature (PVT) measurements can be performed to define physical properties of hydrocarbon reservoir fluids (gases, liquids, and occasionally solids). These measurements can be performed in large, fixed laboratories employing a number of individual pieces of equipment. Early (and some current) PVT cells utilized mercury as a pressurizing and mixing medium within a temperature controlled pressure vessel. Mercury-free units were developed in the early 1990's using either a floating piston or a mechanical screw to change sample volume and thereby, pressure. Both of these types of vessels used mechanical stirring to mix the contained sample. Traditional and currently commercially available PVT cells typically have "windows" to allow viewing of the cell's contents for phase determination and volume measurement and are typically limited to pressure ratings less than 15,000 pounds per square inch (psi).

SUMMARY

An integrated, portable system with the ability to perform multiple suites of analyses typically requiring several instruments can be used to perform fixed lab quality PVT measurements.

In one aspect, pressure-volume-temperature testing systems include: a portable environmental control chamber a first pressure vessel disposed inside the portable environmental control chamber; a second pressure vessel disposed inside the portable environmental control chamber, the second pressure vessel in hydraulic communication with the first pressure vessel; a viscometer configured to measure the viscosity of fluid flowing between the first pressure vessel and the second pressure vessel; and an optics system configured to measure optical properties of the fluid flowing between the first pressure vessel and the second pressure vessel. Embodiments of the systems can include the following features alone or in combination.

In some embodiments, the viscometer comprises a capillary viscometer located such that the fluid flowing between the first pressure vessel and the second pressure vessel flows through the capillary viscometer. In some cases, the viscometer comprises two quartz gauges operable to measure temperature and pressure of fluid on either side of capillary tubing (e.g., a first quartz gauge on one side of capillary tubing and a second quartz gauge on another side of the capillary tubing).

In some embodiments, the optics system comprises a spectrophotometer optically coupled to an optics bock with fiber optic cables, the optics block located such that the fluid flowing between the first pressure vessel and the second pressure vessel flows through the optics block.

In some embodiments, the first and second pressure vessels comprise pistons separating sample fluid from hydraulic fluid. In some eases, the systems also include a automated control system operable to electronically communicate with the viscometer; with the optics system; and with pumps in hydraulic communication with first and second pressure vessels. In seine embodiments, testing systems also include an automated control system operable to determine specific hydrocarbon phase volumes based at least in part on data from the optics system. The automated control system can be operable to control the pumps during PVT experiments including: Constant composition expansion (CCE). Differential liberation (DLE), Constant volume depletion (CVD), Separator test(s), Viscosity measurements, Wax appearance temperature (WAT), and Asphaltene onset experiments based on data from the pumps, optics system, and viscometer without requiring operator input beyond inputting initial experiment parameters. The automated control system can be operable to perform more than one of the experiments concurrently.

In some embodiments, the portable environmental control chamber comprises a programmable oven operable to control the temperature of fluid in the pressure vessels. In some cases, the environmental control chamber is operable to provide temperatures ranging from 0° to 350° F. and to allow isothermal and programmed ramp temperature control.

In some embodiments, the pressure vessels are rotatable within the portable environmental control chamber. The pressure vessels can be rotatable within the portable environmental control chamber to control vertical positions of the first and second pressure vessels relative to conduits connecting the first pressure vessel to the second pressure vessel.

In some embodiments, the first and second pressure vessels and associated fittings and connections are configured to contain pressures of up to 20,000 psia.

In some embodiments, the systems are configured to provide pressure, temperature, and volumetric accuracy and control to within 2% overall.

In one aspect, a method of testing fluids includes: transporting a testing system to a site where a sample fluid is withdrawn from a subterranean formation; controlling temperature and pressure of the sample fluid in the testing system; equilibrating the sample fluid by transferring the sample fluid between a first pressure vessel and a second pressure vessel in hydraulic communication with the first pressure vessel; measuring viscosity of fluid flowing between the first pressure vessel and the second pressure vessel while equilibrating the sample fluid; and measuring optical properties of the fluid flowing between the first pressure vessel and the second pressure vessel while equilibrating the sample fluid.

In some embodiments, controlling the temperature of the sample fluid comprises controlling the temperature of the sample fluid using a portable environmental control chamber containing the first and second pressure vessels. In some cases, methods also include adjustably controlling orientation of the first and second pressure vessels within the portable environmental control chamber. In some cases, methods also include using the portable environmental control chamber to decrease the temperature of the sample fluid at a specified rate.

In some embodiments, methods also include identifying phase change boundaries in the sample fluid based on changes in the optical properties of portions of the sample fluid.

In some embodiments, methods also include performing at least two of a constant composition expansion test, a differential liberation test, viscosity; a constant volume depletion test, a separation test, a wax appearance temperature test, and an asphaltene onset test concurrently on fluid in the first and second pressure vessels.

In some embodiments, methods also include controlling the vertical orientation of the first and second pressure vessels to sub-sampling, analysis, or both of a specific hydrocarbon phase.

The small size of these PVT cells enables use of the systems described above in mobile laboratories.

Using a capillary viscometer for phase determination and volume measurements, can allow systems to be configured to achieve pressure ratings excess of 15,000 psi (e.g., up to 20,000 psi).

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 2A-2F are views of pressure cells of an analysis device.

Like reference symbols in the various drawings indicate like elements.

DETAILED DESCRIPTION

Figure 1:
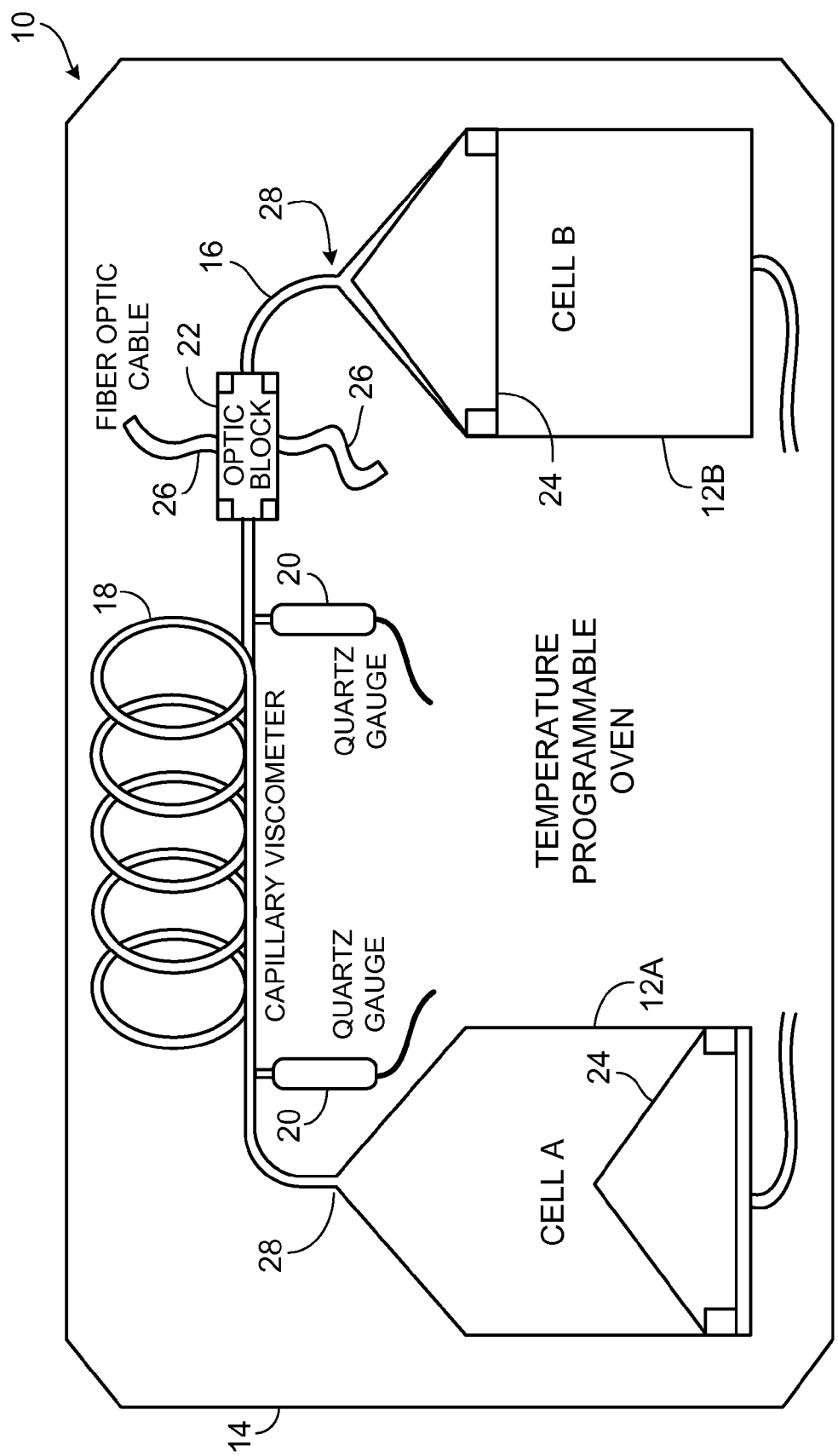
FIG. 1 is a schematic view of an analysis device.
Figure 2C:
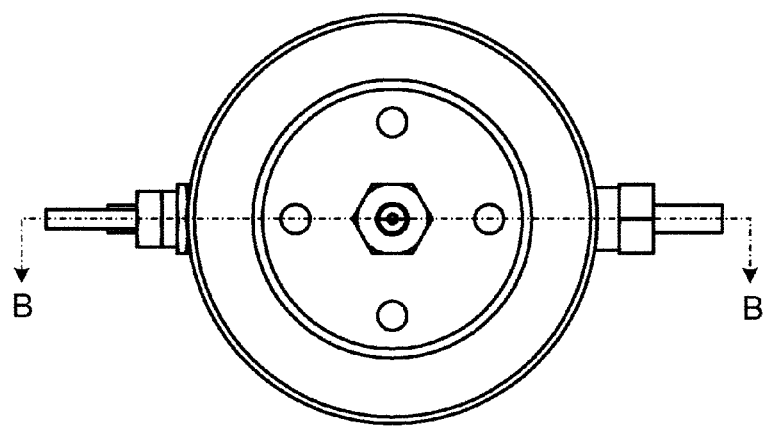
Figure 2E:
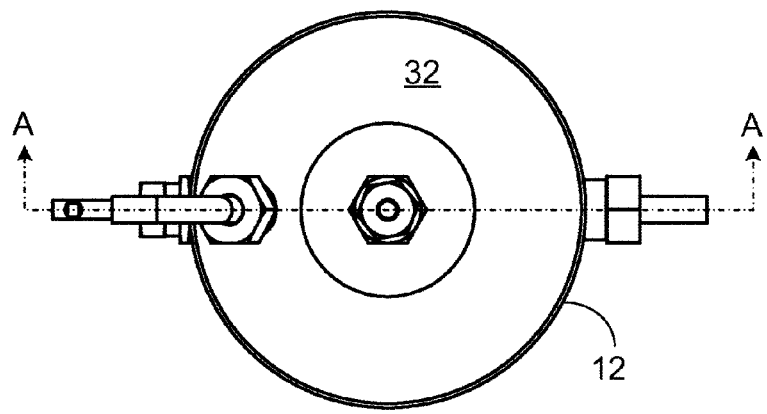
Figure 2D:
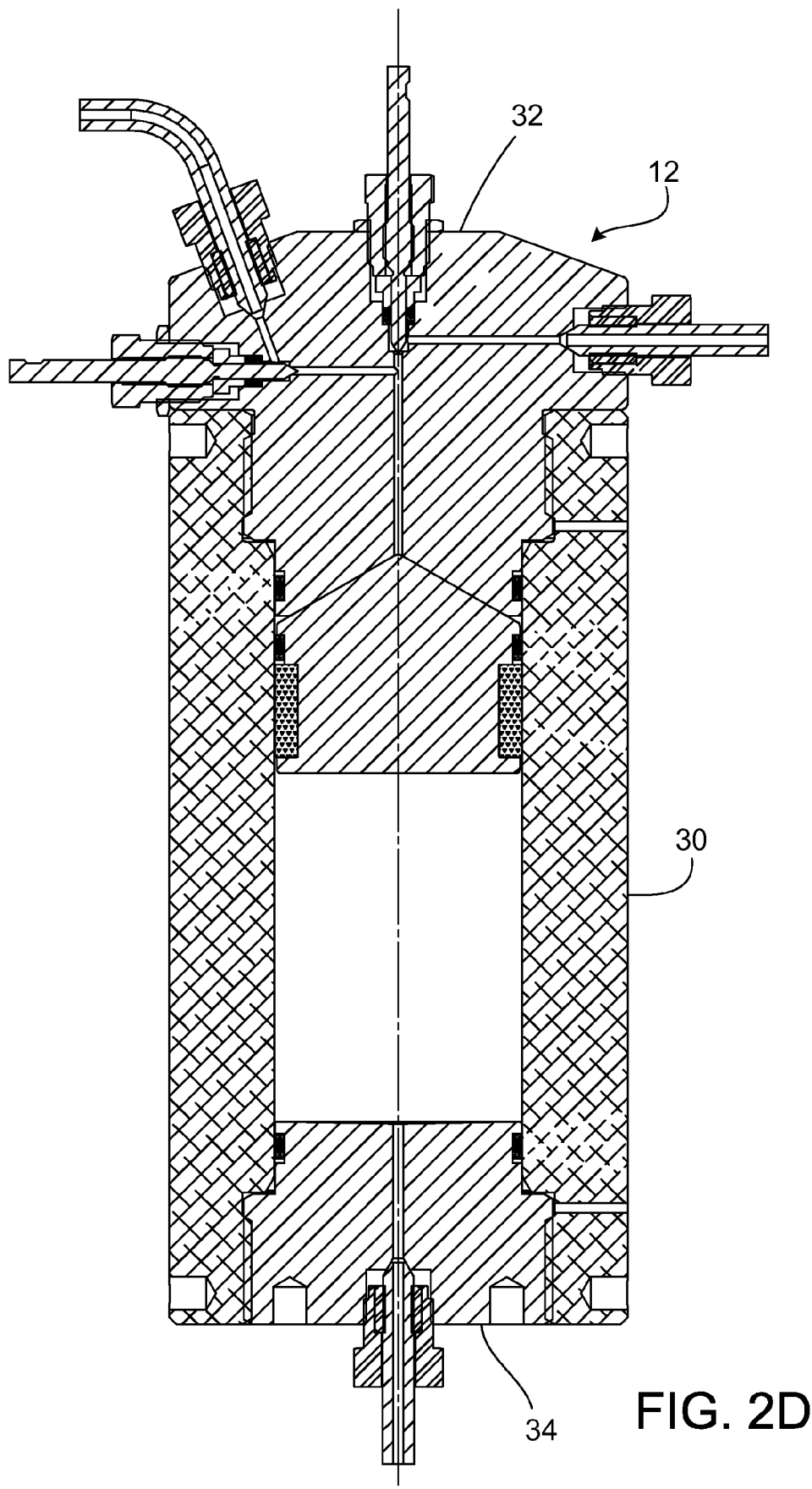
Figure 2F:
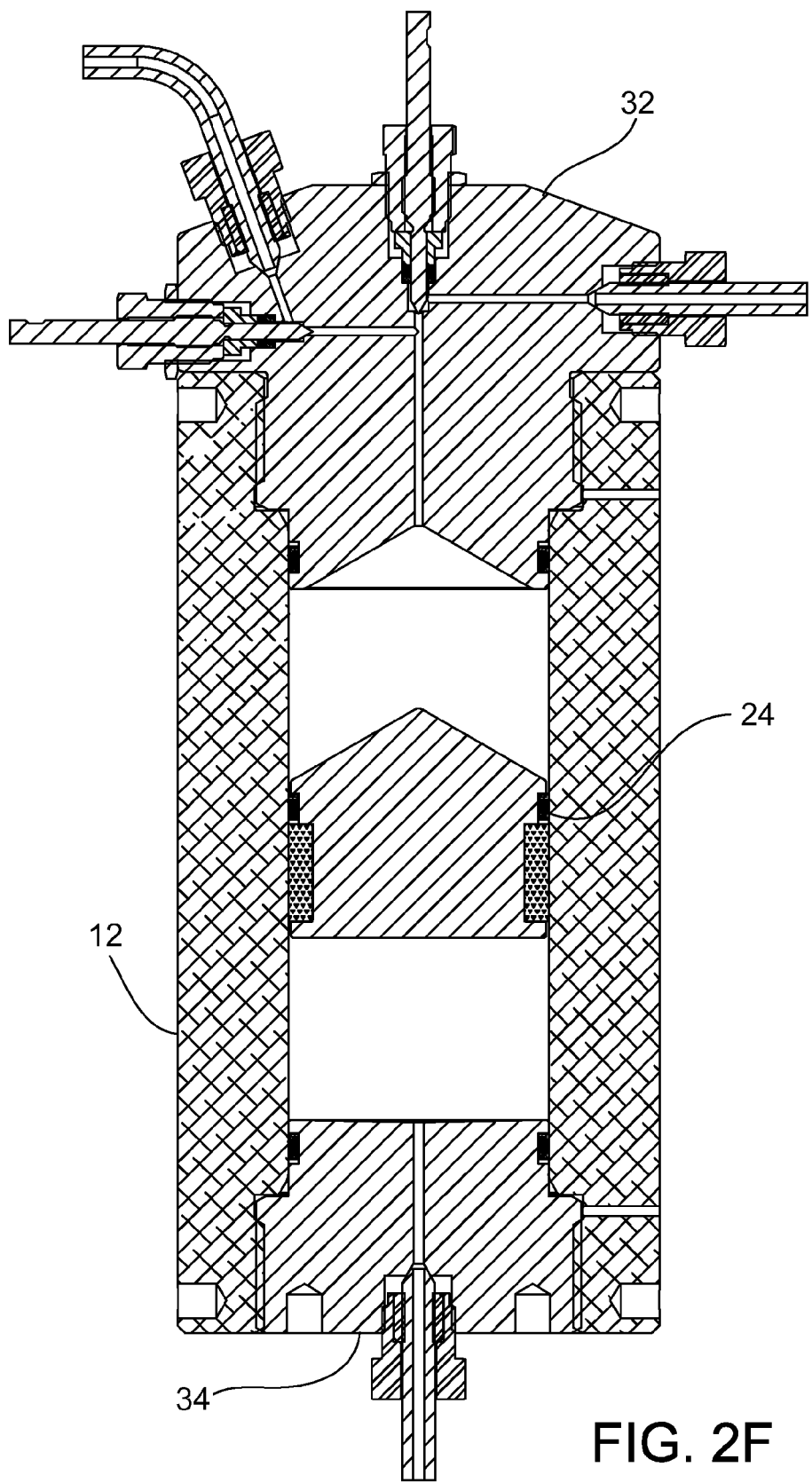
Figure 3A:
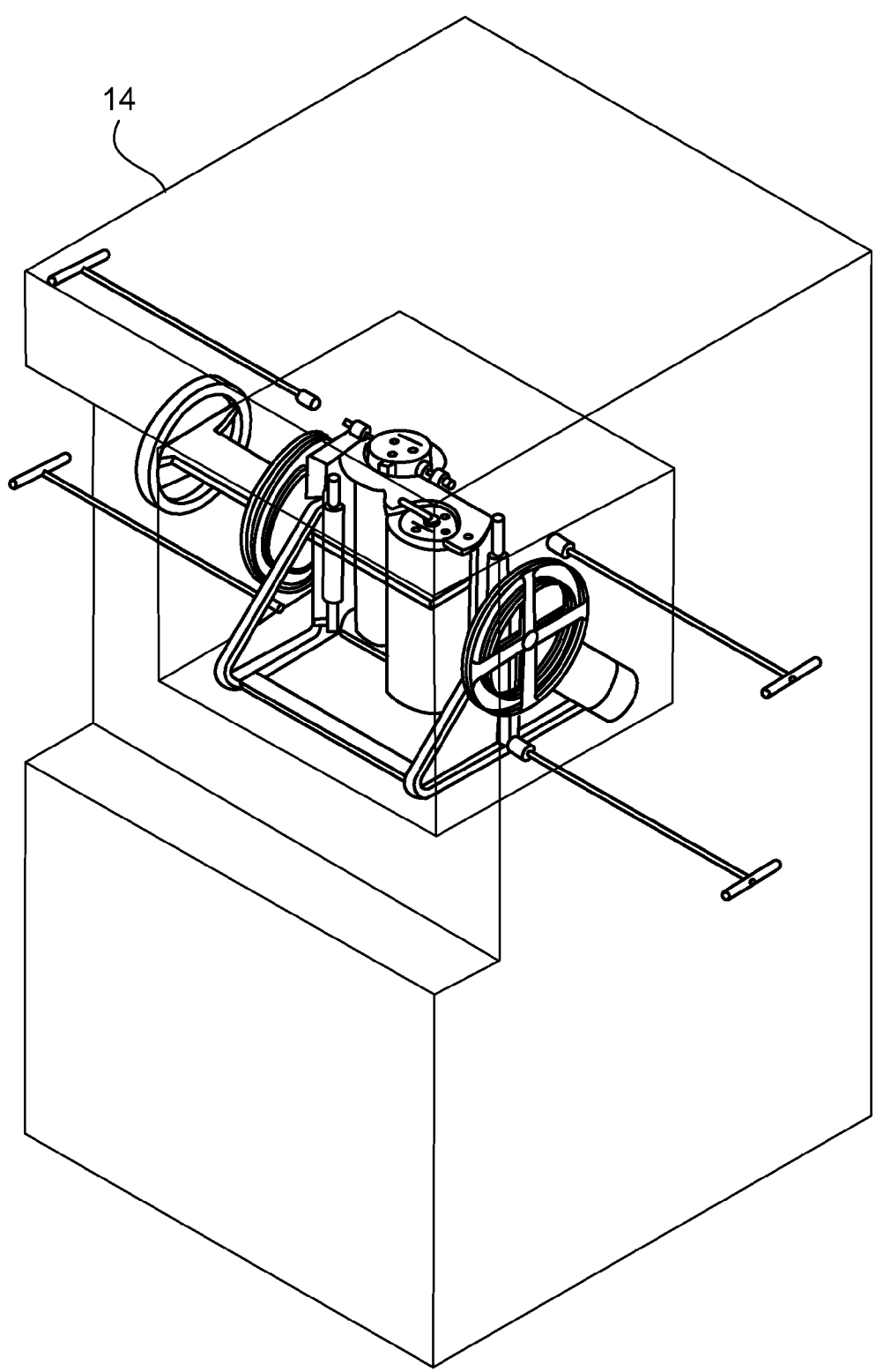
FIGS. 3A-3D are, respectively, perspective, side, top, and front views of an embodiment of an analysis device.
Figure 3B:
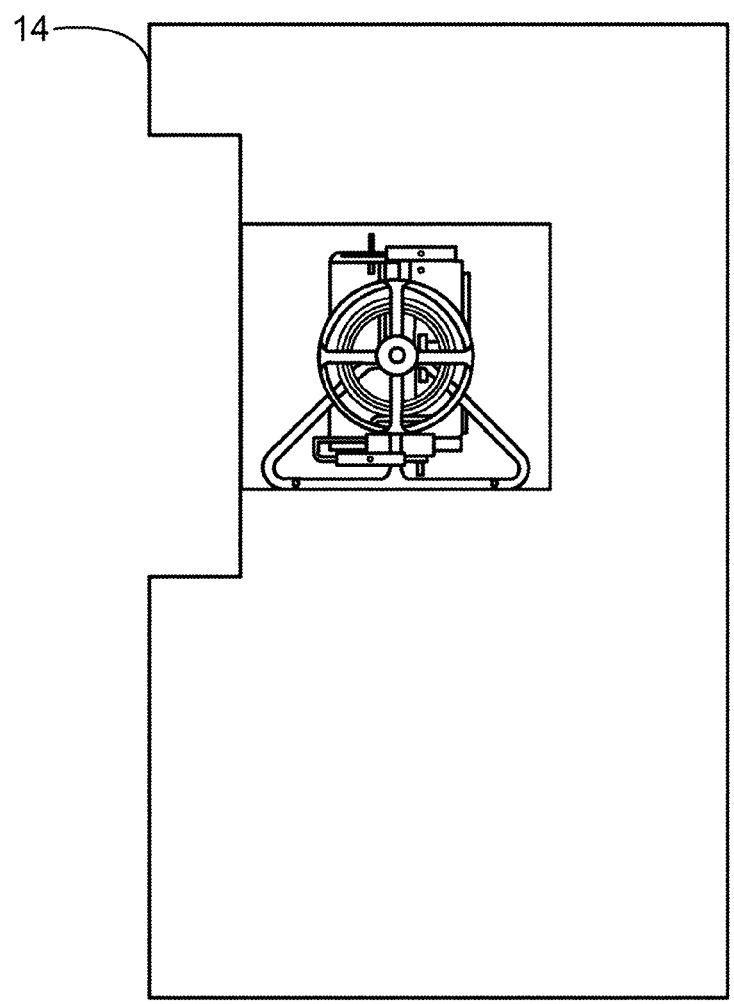
Figure 3C:
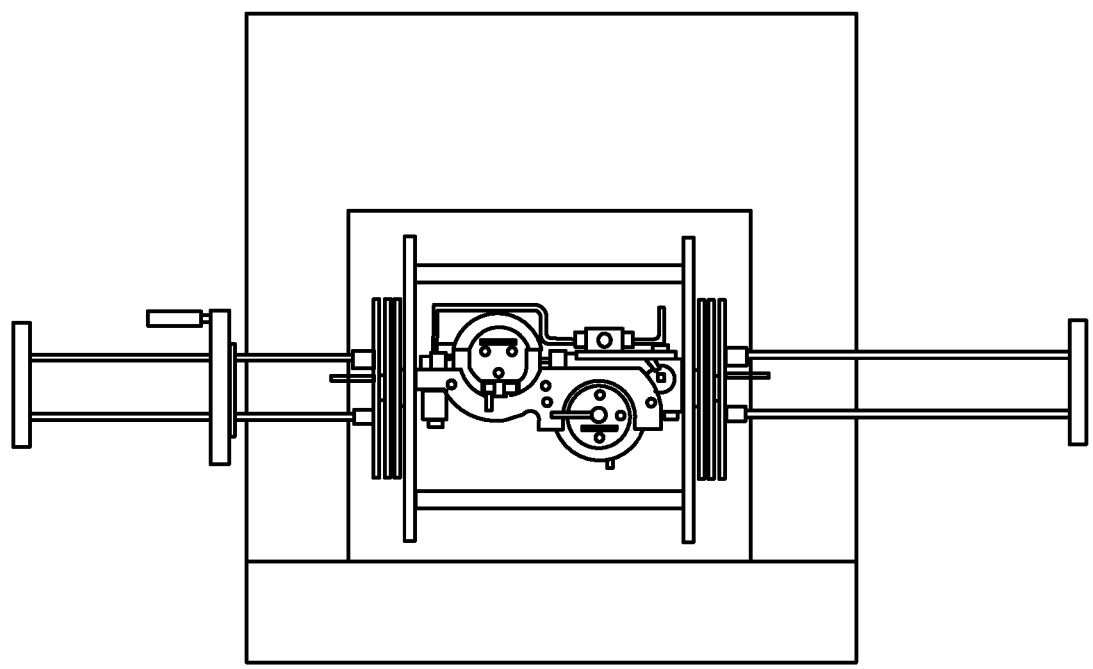
Figure 3D:
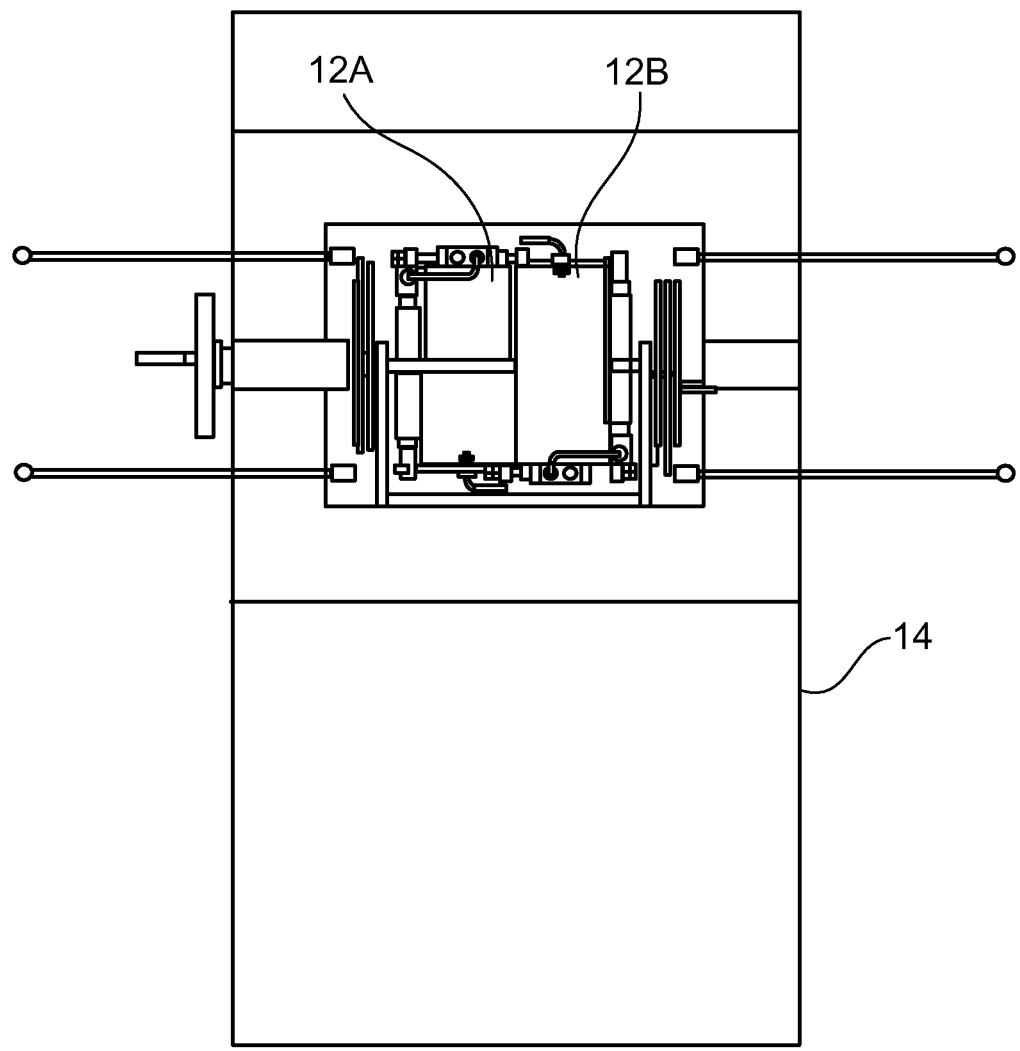

Referring to FIG. 1, a mini-PVT system 10 illustrates a compact system capable of high pressures and temperatures for performance of pressure-volume-temperature measurements to define physical properties of hydrocarbon reservoir fluids (gases, liquids, and occasionally solids). The system 10 includes two pressure vessels or cells 12A, 12B inside an environmental control chamber 14. Tubing 16, including a capillary viscometer IS, hydraulically connects the two cells 12A, 12B. The capillary viscometer includes mechanisms for measuring pressure (e.g., quartz pressure gauges) 20 located on each side of capillary tubing of known dimensions. The system 10 can also include an optics block 22 configured to measure optical properties of fluids flowing through the tubing 16 (e.g., to detect phase interfaces and/or the presence of suspended solids).

Each of the two cells 12A, 12B contains a floating piston 24. The cells 12A, 12B are configured to contain small volumes of fluids and associated material such as, for example, suspended solids at high pressures. For example, the cells 12A, 12B can comprise 200 cc capacity chambers, rated to 20,000 psi. Sample chamber volume and thereby, pressure is controlled by either injecting or withdrawing hydraulic fluid (typically water) on the backside of the floating piston(s) 24 utilizing computer-controlled, high accuracy pumps (not shown). In performing PVT measurements as described in more detail below, it is desirable that the pumps be operable: to run for long periods of time (e.g., more than 6 hours, more than 12 hours, or more than 24 hours); to transfer at least 10 cc per minute (e.g., between about 50 and about 100 cm.sup.3 per minute); and to accurately measure volumes (e.g., to within about 0.1 cm.sup.3). The pump can be used at much slower rates but the pump rate(s) is preferred to be precise as viscosity calculation requires this value.

FIGS. 2A-2F illustrate an embodiment of cells 12A/B. In this embodiment, the cell 12A/B includes a hollow cylindrical body 30 with an upper end cap 32 and a lower end cap 34 sealing piston 24 within the body 30. The lower end cap 34 receives a hydraulic line used to control the position of the piston 24. The upper end cap 32 receives various lines used to transfer fluid between cells 12A/B, to inject sample fluids into the system 10, and to inject gases into the system 10.

Mixing of fluids in the system 10, and therefore equilibrium, are achieved by physically pushing the sample fluid back and forth between the chambers while maintaining desired pressure and total sample volume within the chambers and associated connections during PVT measurements as described in more detail below. This approach to mixing fluids allows system 10 to concurrently and, in some instances, simultaneously measure fluid viscosity and phase volumes during mixing. In certain instances, this approach can achieve phase equilibrium more quickly than single cell PVT systems in which sample mixing is performed by either physically agitating (rocking) the cell or via, is an internal mechanical mixer. In addition, use of the optics block 22 to detect interfaces between different fluids can allow the system 10 to be operated at higher pressures than systems that include "windows" to allow viewing of the cell's contents for phase determination and volume measurement.

Using floating pistons 24 allows system 10 to readily transfer gases and/or liquids. In some embodiments, components of system 10 including the cells 12A, 12B pivotably mounted such that the cells 12A, 12B can be rotated to and fixed in multiple orientations (e.g., with cells 12A, 12B positioned such that pistons 24 are located below tubing inlets 28 as shown in FIG. 1 or with cells 12A, 12B positioned such that pistons 24 are located above tubing inlets 28). Depending on the orientation of the cells 12A, 12B, the system 10 can preferentially transfer gases or transfer liquids. This feature can also be used to drive gas into solution more readily. For example, transferring fluids between cells 12A, 12B with cells 12A, 12B positioned such that pistons 24 are located above tubing inlets 28 results in the gas phase bubbling through the liquid phase during the mixing process. FIGS. 3A-3D, respectively, perspective, side, top, and front views, illustrate a system 10 in which system components including the cells 12A, 12B pivotably mounted such that the cells 12A, 12B can be rotated to and fixed in multiple orientations. These figures do not show the door used to close the environmental control chamber 14.

The capillary viscometer 18 disposed between the individual chambers 12A, 12B of the system 10 is a capillary tube of a known length and internal diameter to allow viscosity and rheology measurements of the sample being analyzed. A selection of capillaries of different lengths and internal diameters are available to accommodate varying sample requirements. For example, various viscometers can be used with liquids whose viscosities range between about 0.01-1000 cP. Such viscometers are commercially available from, for example, Vinci Technologies, Nanterre (Paris), France and Chandler Engineering, Tulsa, Okla. High accuracy quartz gauges 20 on either end of the capillary viscometer 18 can measurement of pressure (individually), pressure drop across the tube (by subtraction of individual values), plus accurately measure temperature. The use of the capillary viscometer 18 disposed between two pressure vessels enables measurement of viscosity simultaneously with other testing. In other types of viscometers such as rolling ball, falling sinker, and electromagnetic viscometers configured as an individual viscosity testing unit, this may not be the case. In addition, while rolling ball, failing sinker, and electromagnetic viscometers can accurately measure a Newtonian fluid's viscosity when properly calibrated, capillary viscometers also allows measurement of non-Newtonian fluids with direct measurements of shear rate and shear strength.

The optics block 22 disposed between the individual sample chambers 12A, 12B allows light transmittance through the fluid whose properties are being measured at testing temperatures and pressures. Such optics blocks are commercially available from, for example, Phoenix Instruments, Splendora (Houston), Tex.

Using fiber optic cables 26 and a spectrophotometer (not shown), changes in light transmittance can communicate fluid property transformation within the analyzed fluid such as phase (gas, liquid, or solid) changes. Correlating the position of phase boundaries with the volumes of fluids transferred as the sample fluid is pushed through the optical block enables calculation of phase boundaries, volumes, and/or onset conditions (e.g., dew point or bubble point). Use of the inline optics block 22 allows system 10 to do without windows inset into the cell body to allow viewing the cell contents to visualize bubble points in oil systems, dew points in gas condensate systems, and phase boundaries, and to calculate specific sample volumes by measuring vertical height changes in a gas/oil interface or piston position allows. In some instances, this configuration can allow system 10 to be used to apply extremely high pressure conditions (e.g., greater than 15,000 psi, up to 20,000 psi, and/or up to 25,000 psi) to the sample.

Figures 4A, 4B:
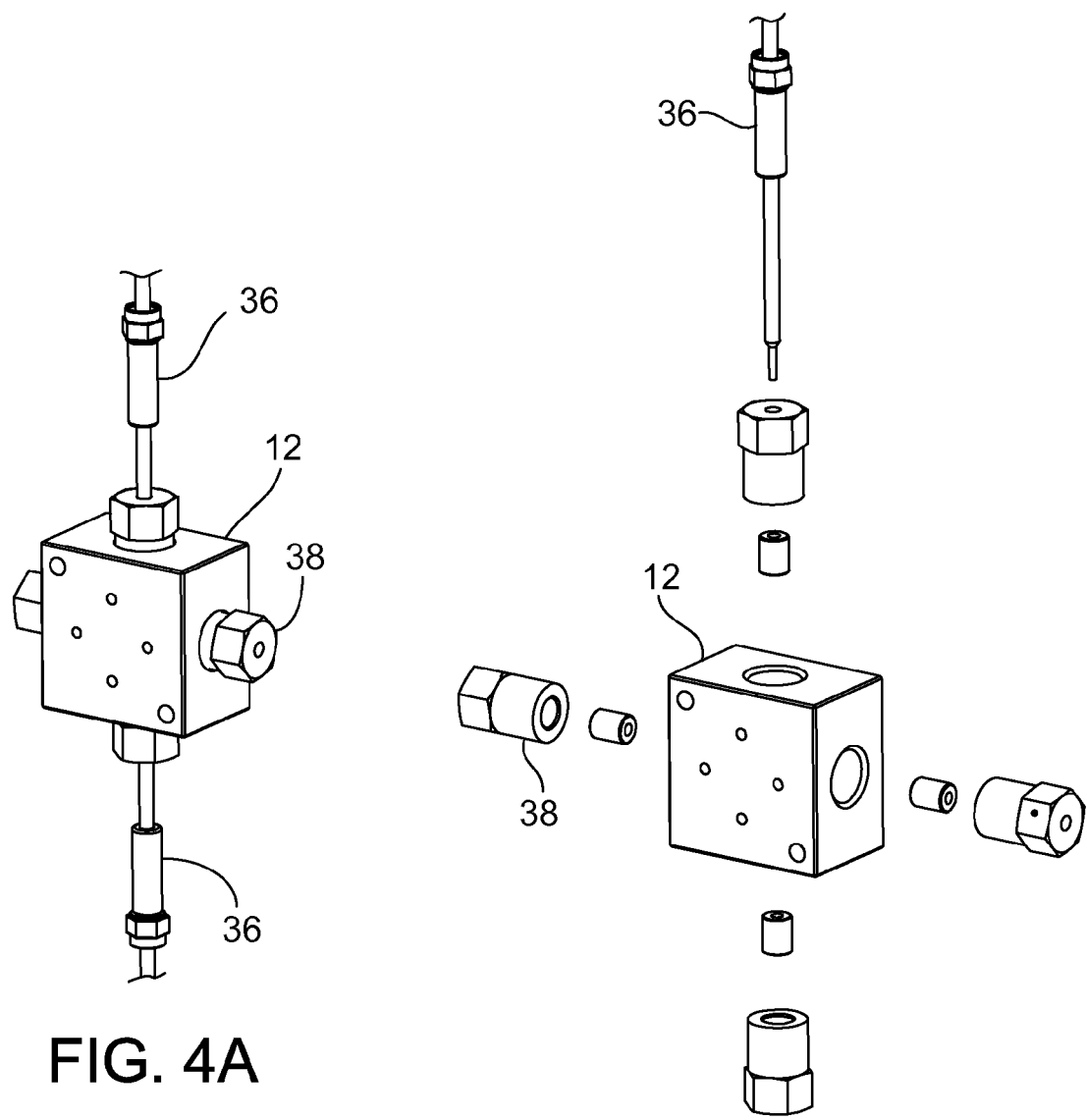
FIGS. 4A and 4B are, respectively, perspective and exploded perspective views of an optical interface detector.

FIGS. 4A and 4B illustrate an embodiment of an optics block with "upper" and "lower" fixtures 36 to receive and engage fiber optics lines 26 and "side" fixtures 38 to receive and engage tubing 16. Relational terms such as "upper" and "lower" are used for ease of description relative to the drawings rather than to imply any absolute position of system components.

In certain instances, the system 10 is configured to improve accuracy and reduce error by limiting equipment dead volume. The hydraulic connections between pressure cells 12A, 12B are configured with shortened lengths and low internal volumes to reduce fitting and tubing capacity between pressure cells 12A, 12B. The pressure cell head assemblies and piston tops can be coned to similar angles to limit the volume between the pressure cell head assemblies and piston tops when seated. The capillary tube viscometer can be configured with low dead volume pressure gauges and small diameter tubing to limit the volume associated with the capillary tube viscometer. Similarly, the optic block for spectrophotometer system can be selected to provide a low dead volume. For example, use of these features reduce the dead volume of the illustrative system 10 to approximately 5 milliliters (e.g., approximately 2.5% of total system volume).

In some embodiments, the environmental control chamber 14 can be a computer controlled oven which can provide controlled temperatures (e.g., between about 0.degree. F. to about 350.degree. F.). The oven can be programmed to provide a temperature ramp at of specified rate of heating or cooling. PVT testing is typically performed at specified temperatures such as reservoir temperature, flow line temperature, or process temperature so accurate temperature control is required. The ability to program temperature ramps allows solids precipitation or crystallization to be investigated. The "environmental chamber" selected, is relatively small and able to readily fit within a Mobile laboratory cabin but, unlike commercially available gas chromatographic (GC) ovens, is large enough to accommodate the pressure vessels 12A, 12B and associated peripheral components. In one embodiment, the unit has dimensions of 24"W.times.44"H.times.26"D and weighs approximately 300 lbs.

The system 10 includes an automated control system configured to operate the system 10 including recognizing fluid equilibrium, accurately setting and reading temperature, pressure, and volume devices all of which can affect the reliability of the data generated. The automated control system can be implemented using hardware, software, or both. System software can be provided as a separate computer program product (e.g., on a CD) that can be installed in the system 10 before use or as a combination of embedded software and hardware. System software executed by the control system can be configured to run testing protocols with as little operator influence as possible and can fully monitor and control pressure, volumetrics, and temperature. Embedded software is configured to control (e.g., maintain or change) the sample volume while pushing gas, liquid, and/or solid from chamber to chamber. During this process, pressure, volume, temperature and spectrographic data are logged allowing calculation of the desired PVT properties. Criterion input within the software are configured to operate the system 10 to quickly achieve equilibrium conditions.

Some PVT experiments are fully automated (e.g., programmable with no operator intervention required), the remaining analyses are programmed to advance to set pause conditions where brief operator involvement must occur. In particular, the system 10 can be configured to perform constant composition expansion experiments, differential liberation experiments, separator test experiments, constant volume depletion experiments, wax appearance temperature experiments, and asphaltene onset pressure experiments with limited or no operator intervention. These software controls and bundling of testing capability can achieve high data quality in short times with the low requirements for operator training. A minimal sample volume requirement for a full suite of PVT experiments is yet an additional bonus.

The automated control system can reduce test times; provide repeatable and reproducible results; achieve a high level of accuracy; and create a non-transcribed, digital record of each experiment. These features can reduce the errors associated with manually operated PVT systems in which lab technicians make subjective judgments (visual or otherwise) regarding the state of equilibrium, liquid levels, and other parameters during the tests. In addition, the technicians must transcribe the data to a laboratory data form or spreadsheet. Subjective judgments and transcription errors are the largest sources of error in commercial laboratories and ultimately mean that many laboratories cannot easily repeat or reproduce results from their tests.

The automated control system may comprise one or more electronic computing devices operable to receive, transmit, process, and store data associated with system 10. Each computer is generally intended to encompass any suitable processing device. Each computer may be any computer or processing device such as, for example, a blade server, a general-purpose personal computer (PC), Macintosh, workstation, Unix-based computer, or any other suitable device. In other words, the present disclosure contemplates computers other than general purpose computers, as well as computers without conventional operating systems. Each computer may be adapted to execute any operating system including Linux, UNIX, Windows Server, or any other suitable operating system.

Each computing device may have memory and a processor. The memory may also be remote and connected through a network. The memory is computer readable media suitable for storing computer program instructions and data. The memory may be any form of non volatile memory, media and memory devices, including by way of example random access memory (RAM), read-only memory (ROM), or other memory devices, such as, e.g., EPROM, EEPROM, and flash memory devices; magnetic disks, e.g., internal hard disks or removable disks; magneto optical disks; and CD ROM and DVD-ROM disks. The memory may store data. The memory may also store software related to and/or executed by any of the computing devices used in system 10.

Each computing device in system 10 may contain a processor that executes instructions and manipulates data to perform the operations of a computing device such as, for example, a central processing unit (CPU), a blade, an application specific integrated circuit (ASIC), or a field-programmable gate array (FPGA). Generally, the processor will be operatively coupled to receive data and/or instructions from, or transfer data to, the memory. The processor and some or all of the data stored in the memory can be supplemented by, or incorporated in, special purpose logic circuitry, such as an application-specific, integrated circuit.

The automated control system may comprise or reference a local, distributed, or hosted computing software. At a high level, computing software is any application, program, module, process, or other software that may access, retrieve, modify, delete, or otherwise manage some information in the memory. One example computing software may be a computer application for performing any suitable experiment by implementing or executing a plurality of steps. Another example of computing software is an application that provides interconnectivity with one or more engines or modules. GUIs, which allow users to input data and interact with the system 10, are another example of computing software.

Regardless of the particular implementation, "software" may include software, firmware, wired or programmed hardware, or any combination thereof as appropriate. Indeed, each of the foregoing software applications may be written or described in any appropriate computer language including C, C++, Java, Visual Basic, assembler, Perl, any suitable version of 4GL as well as others. Further, one or more processes associated with these applications may be stored, referenced, or executed remotely. Moreover, each of these software applications may be a child or sub-module of another software module or enterprise application (not illustrated) without departing from the scope of this disclosure.

A GUI is a computer program hosted on a client. A GUI comprises a graphical user interface operable to allow an operator of system 10 to interface with at least a portion or system 10 for any suitable purpose, such as viewing experiment parameters or other data. Generally, a GUI provides the particular user with an efficient and user-friendly presentation of data provided by or communicated within system 10. It should be understood that the term graphical user interface may be used in the singular or in the plural to describe one or more graphical user interfaces and each of the displays of a particular graphical user interface. Indeed, reference to the GUI may indicate a reference to the front-end or a component of an application, as well as the particular interface accessible via a client, as appropriate, without departing from the scope of this disclosure. Therefore, a GUI contemplates any graphical user interface, such as a generic web browser or touchscreen, that processes information in system 10 and efficiently presents the results to the user.

Various testing procedures can be performed using system 10. For example, samples of subsurface fluids can be collected during open hole logging, transferred into sample cylinders, and transferred, along with samples of whole mud and mud filtrate, to an onsite mobile laboratory for use in a PVT study.

Figure 5:
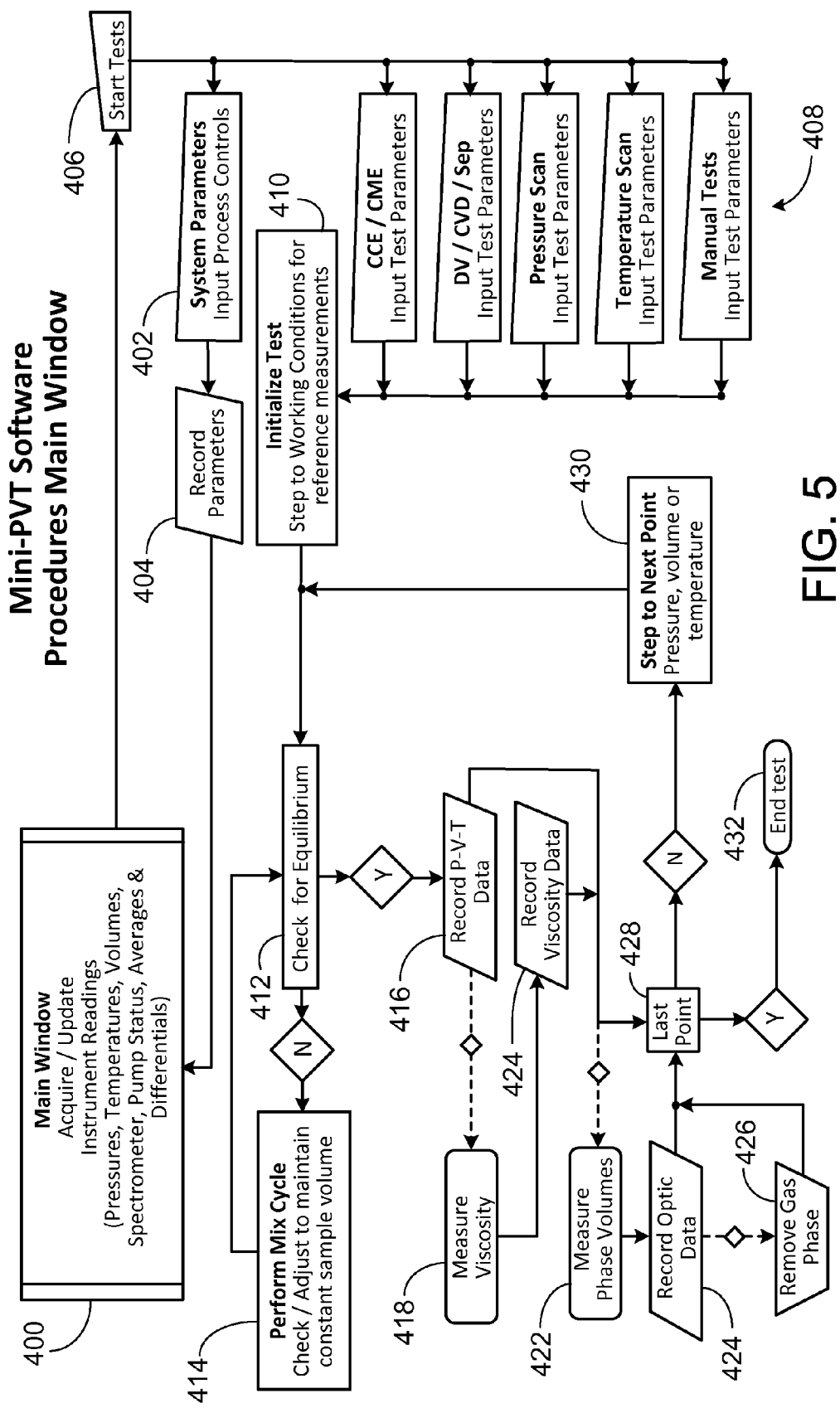
FIG. 5 is a high-level flowchart of controller logic that can be used to operate the analysis device of FIG. 1.

FIG. 5 illustrates the general process of an illustrative embodiment of an automated control system for system 10. Upon startup, the automated control system acquires and/or updates instrument readings including, for example, system pressures, temperatures, volumes, spectrometer status, and pump status (400). During operation, system parameters are monitored (402) and recorded (404). To start a test (406), an operator selects the experiments to be performed and inputs the test parameters into the automated control system (408). For example, for a constant composition expansion (CCE) experiment, the operator enters the estimated saturation pressure, minimum pressure, maximum expansion. The automated control system that initializes the test (410) by bringing the system 10 to working conditions for initial reference measurements. The samples are typically initially restored into a single-phase reservoir fluid. For example, a sample can be transferred into cells 12A, 12B of system 10 and the environmental control chamber 14 can be, used to heat the sample to reported reservoir temperatures. The hydraulic pumps can be operated to pressurize the sample to above reservoir pressures and then to mix the sample by transferring the sample back and forth between cells 12A, 12B until equilibrium conditions are achieved. This allows any free gas, condensed liquids, or crystallized solids to be "restored" into a single-phase reservoir fluid.

The automated control system then checks if the sample being tested is at equilibrium (412). Before volumetric data is recorded during a PVT test, the fluid being tested should be in a state of thermodynamic equilibrium. Equilibrium times are significantly affected by the type of sample (oil, gas, or brine); system temperature; system pressure; and the number of phases. The automated control system continually monitors pressure, volume and temperature to determine when the fluid is in thermodynamic equilibrium. The automated control system calculates a trailing median value for pressure and/or volume for a specified number of readings (e.g., ?# readings) and evaluates the results over a pre-defined 'window' of time (e.g., ?time). If the readings are constant (within +/− a prescribed amount, for example, %?), the system is considered to be in equilibrium. This approach of automatically assessing whether equilibrium conditions have been achieved by specifying a desired maximum pressure or volume change per time or mix increment avoids the months of training required to teach a lab technician how to identify true thermodynamic equilibrium over a wide range of sample types and fluid pressures/temperatures and also provides objective, reproducible results.

If the system 10 has not achieved thermodynamic equilibrium, the automated control system performs a mix cycle (414) as described above including checking and adjusting the positions of the pistons in the pressure cells maintain a constant sample volume. If the system 10 has achieved thermodynamic equilibrium, the automate control system of records pressure-volume-temperature data (416).

The automated control system can calculate viscosity of the sample (418) on an ongoing basis based on the capillary tube dimensions, the differential pressure across the capillary viscometer 18 measured using the quartz gauges 20, and the velocity of fluid flow through the capillary viscometer 18. The automated control system can record the viscosity of the sample (420) at specified intervals and/or when the pressure-volume-temperature data is being recorded. Laminar flow or near-laminar flow can improve the accuracy of viscosity measurements (e.g., if the sample fluid is in turbulent or vortex flow, the viscosities measured can be in error by as much as 50%). To prevent this error, the automated control system calculates benchmark parameters such as Reynold's Number, Dean's Number, and apparent viscosity while the test is running and displays the results on the screen for the operator. If the sample is flowing in the wrong regime during a test, the software will warn the operator and allow him to adjust the pump rates or automatically adjust the pump rates. This can provide more accurate viscosity measurements than viscometers or labs that do not monitor these properties in 'real' time.

The automated control system uses optical detection and differential pressure data to identify when the first bubble of gas forms in a liquid (bubblepoint); the first drop of liquid condenses from a gas (dewpoint); and/or first organic solid forms (e.g., wax or asphalt). The automated control system uses a spectrometer to monitor absorbance of light in the UV/Vis range of wavelengths. The light absorbance pattern changes abruptly when phase changes occur or when organic solids form. When phase changes occur, automated control system measures phase volumes (422), records optical data (424), and, as appropriate, removes the gas phase from the system 10 (426).

The automated control system checks if this is the last point in experiment (428). If not, the automated control system steps to the next set point (430) and repeats the test cycle. If so, the automated control system concludes the test (432).

The automated control system also records the change in the differential pressure across the capillary viscometer. Should the differential pressure exceed a pre-set threshold as when wax or asphalt forms), the system will stop the experiment, return the fluid to the reference cell and restore the fluid to the original conditions in preparation for the next test. The combination of optics and differential pressure for redundancy and the use of high-precision gauges results in a high degree of accuracy.

Figure 6:
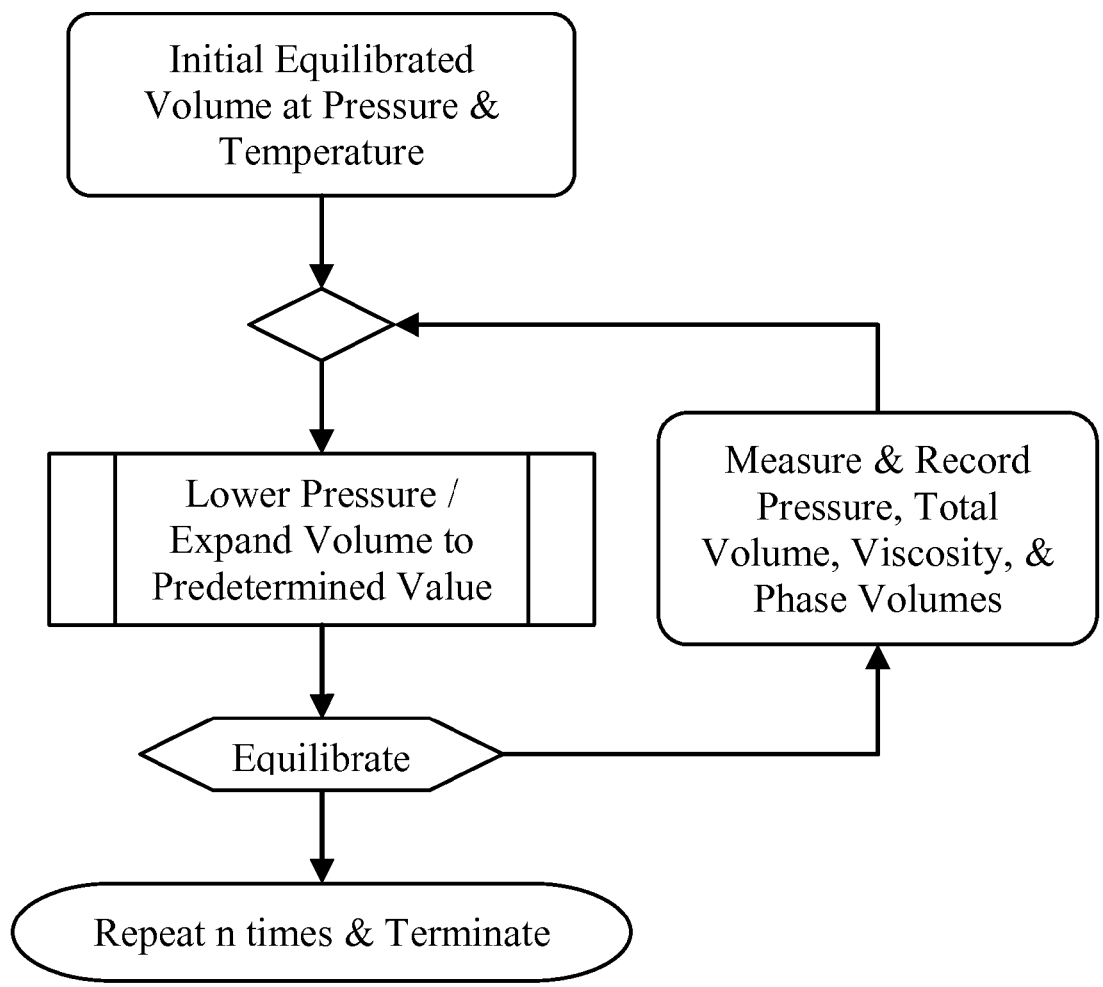
FIG. 6 is a flowchart of a constant composition expansion experiment.

Using the exemplary process illustrated in FIG. 6, the system 10 can be used to perform a constant composition expansion (CCE) test in which the reservoir fluid in the cells 12A, 12B is subjected to a constant composition expansion at reported reservoir temperatures. The CCE experiment is performed by expanding a fluid in pre-defined volume increments. As the volume expands, the fluid pressure drops. Liquids collected from subsurface reservoirs contain 'solution' gas—i.e., gas that is dissolved in the liquid at high pressures and temperatures. Because of the presence of solution gas, using a constant volume increment to expand the sample does not produce an optimum distribution of data points. Similarly, retrograde gas condensates are not best analyzed using a constant volume increment. To achieve the optimum distribution, the automated control system employs an algorithm that combines a non-normal statistical distribution function with a logarithmic equation. The algorithm generates a distribution of data points that are concentrated around the estimated saturation pressure (i.e., bubblepoint or dewpoint) while taking progressively (logarithmically) larger volume steps for the two-phase portion of the CCE measurements.

The operator provides the automated control system with input parameters including, for example, estimated saturation pressure, minimum pressure, maximum expansion. During this process, the fluid is expanded from a pressure above reservoir conditions to, for example, 250 psia while total fluid volume above and below the bubble point (i.e., the pressure at which gas is produced from solution) is recorded. The bubble point can be identified using the optical block 22 and spectrophotometer to identify changes in the optical properties of the sample fluid and/or by a sharp break in the overall compressibility of the fluid in the system. The reservoir fluid can be identified as under-saturated, saturated, or over-saturated at reservoir conditions by comparing the bubble point with observed reservoir conditions. Sample relative volume, single-phase compressibility, two-phase Y-function, and single-phase density can also be calculated as functions of pressure.

Figure 7A:
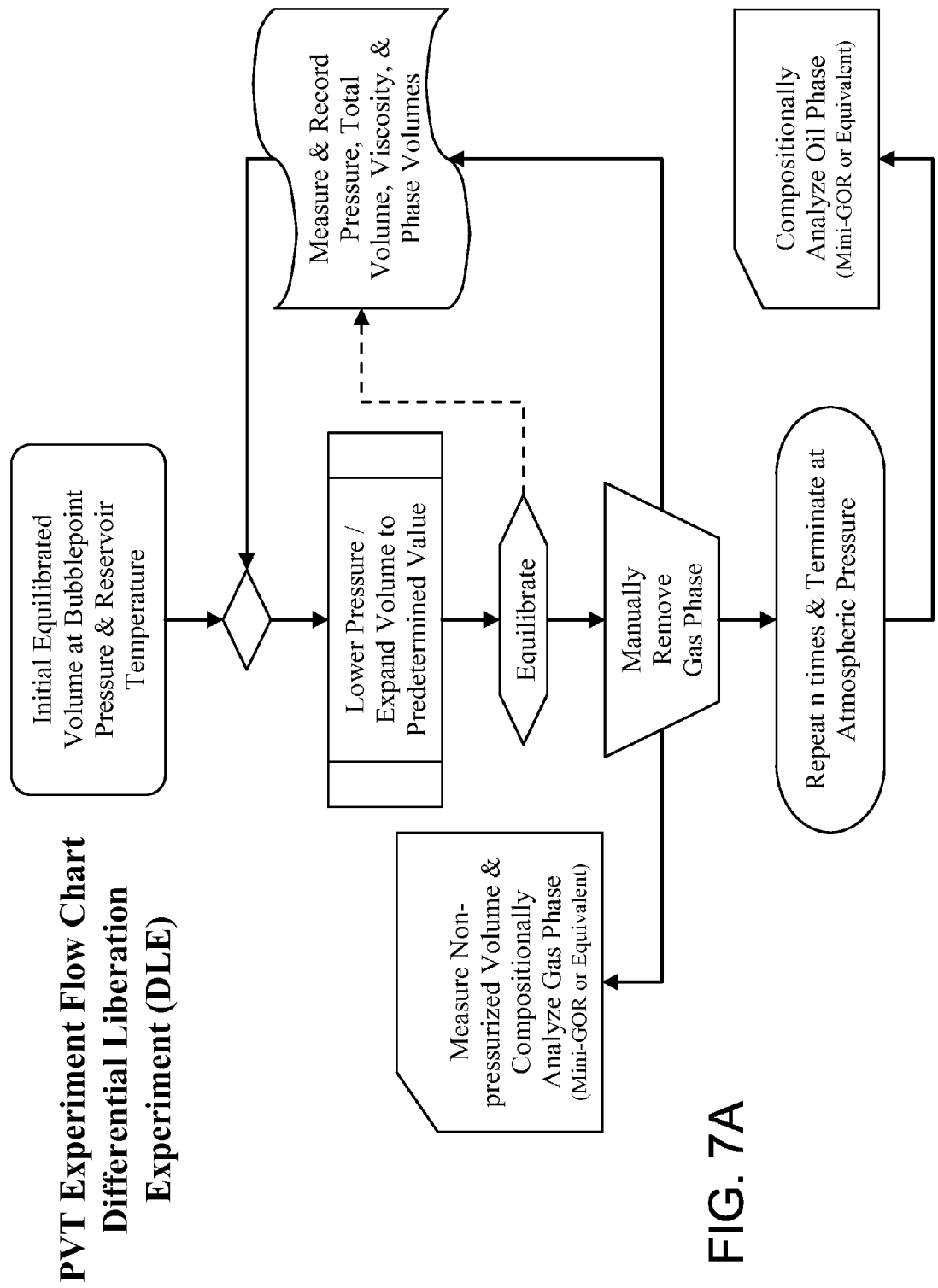
FIG. 7A is a flowchart of a differential liberation experiment.
Figure 7B:
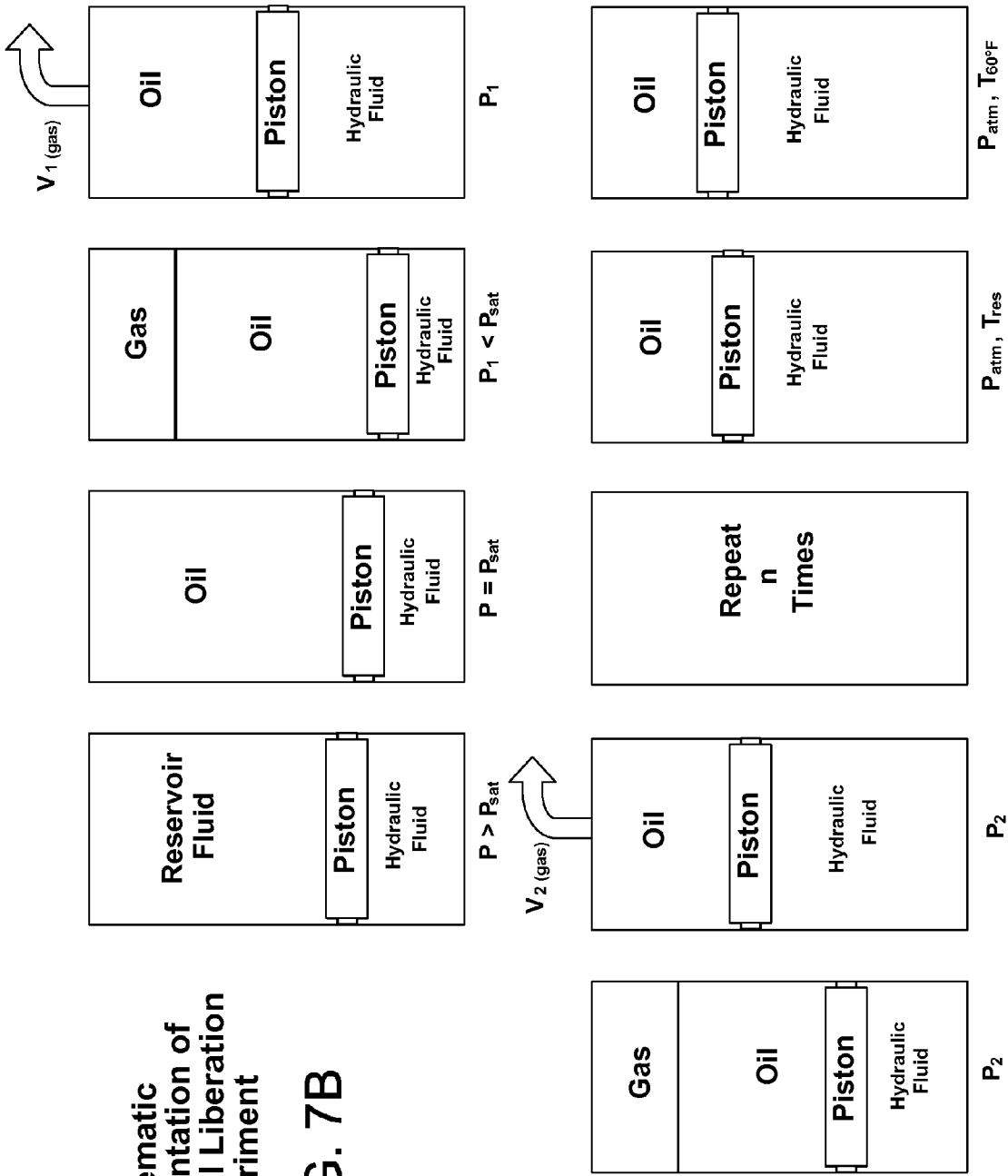
FIG. 7B is a schematic representation of a pressure cell during different stages of a differential liberation experiment.

Using the exemplary process illustrated in FIGS. 7A and 7B, the system 10 can be used to perform a differential liberation experiment (DLE) to simulate the effects of depletion of the reservoir below its bubble point. The operator provides the automated control system with input parameters including, for example, pressure increments. The sample fluid is initially subjected to observed reservoir temperatures and pressure at or slightly above the bubble point observed during the CCE test. At stepwise pressure drops between bubble point and atmospheric pressure, the sample is mixed to equilibrate gas and liquid phases. After equilibration, phase volumes are measured, the equilibrium gas phase is removed with the composition of removed gas phase being measured using compositional analysis by extended gas chromatography (GPA 2286 method), and liquid phase shrinkage is measured using the system 10. These measurements allow calculation of oil volume factor (Bo), gas/oil ratio (Rs), gas volume factor (Bg), gas gravity, gas Z-factor, and oil density. The gas compositions along with the composition of the residual oil permit calculation of the original reservoir fluid composition by material balance.

Figure 8A:
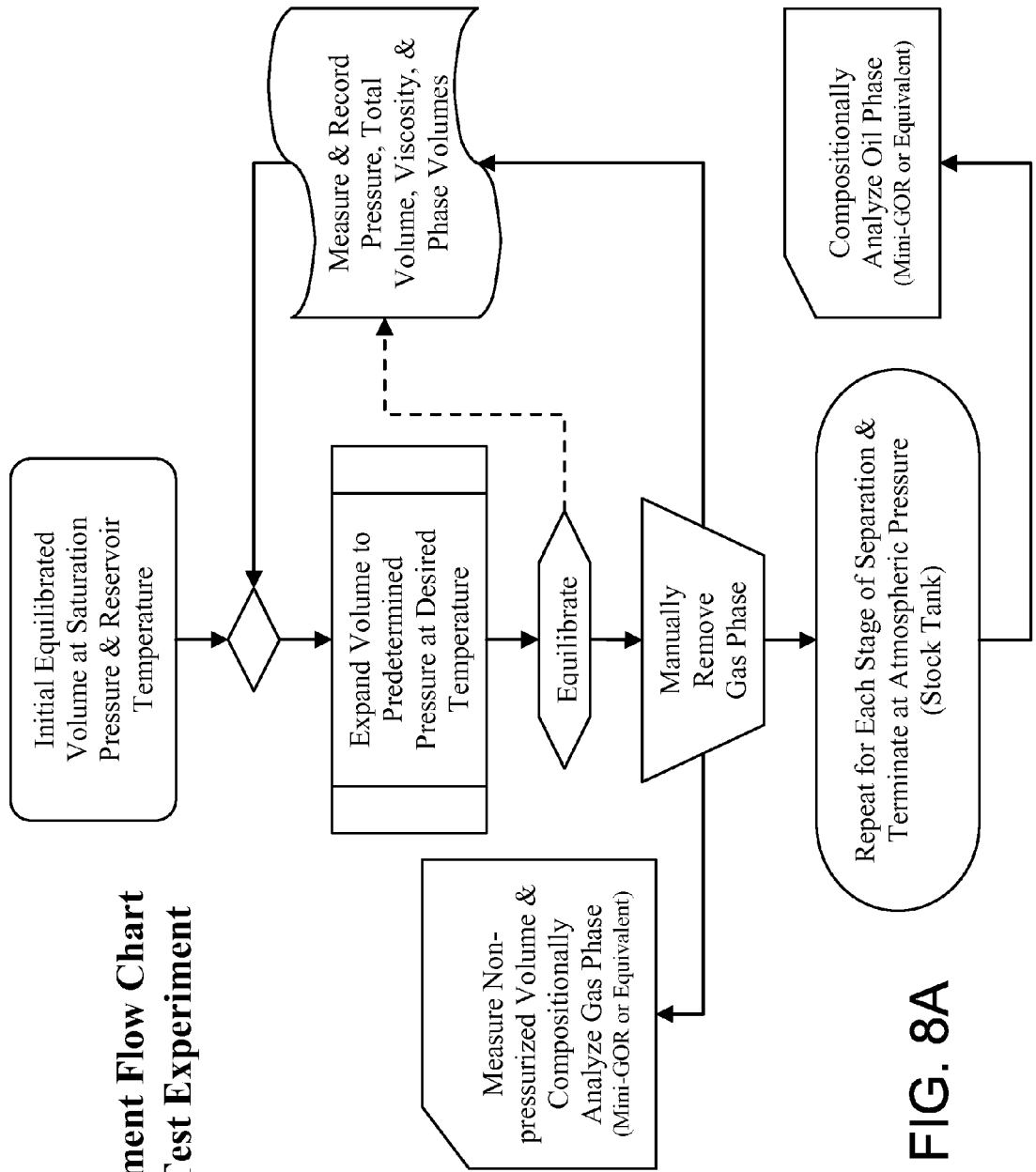
FIG. 8A is a flowchart of a separator test experiment.
Figure 8B:
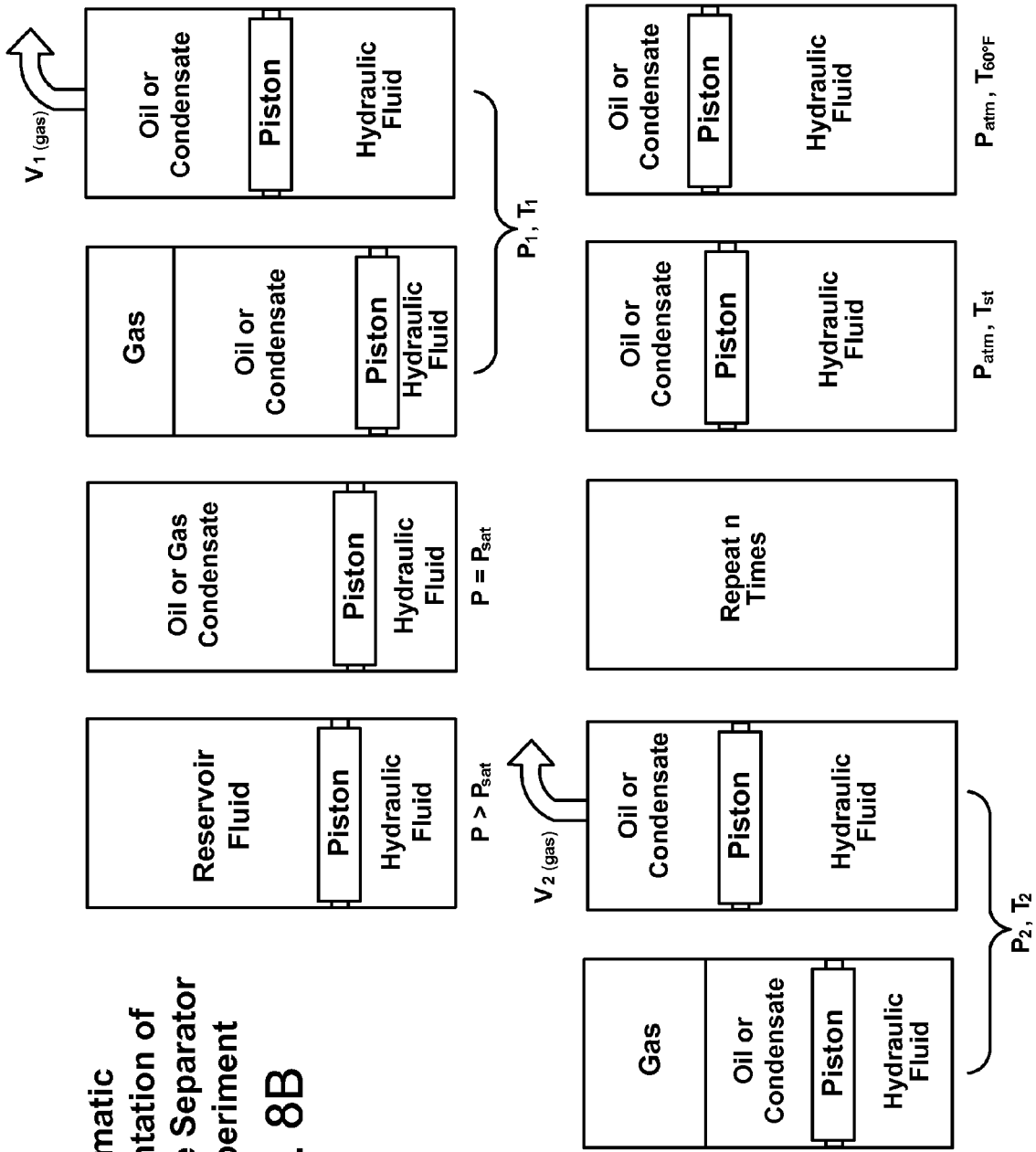
FIG. 8B is a schematic representation of a pressure cell during different stages of a separator test experiment.

Using the exemplary process illustrated in FIGS. 8A and 8B, the reservoir fluid sample can also be subjected to a multi-stage separator test at planned process conditions to determine gas/oil ratio, formation volume factor, oil shrinkage factor, and produced gas compositions (e.g., at surface conditions). The operator provides the automated control system with input parameters including, for example, pressure/temperature increments. The system 10 is used to equilibrate the sample fluid at various temperature and pressure conditions after which the gas phase is removed. Measurement of the stock tank oil composition allows material balance calculation of the reservoir fluid as a data quality check. For example, the vent lines can be directly connected to a compositional analysis system which, for example, implements a method of analyzing a composition including live crude includes separating the composition into a vapor phase and a liquid phase. A composition of the vapor phase can be determined with a gas chromatograph. At least a portion of the liquid phase can be deposited in a vessel, and a headspace vapor phase can be collected from the vessel. A composition of the headspace vapor can be determined with the gas chromatograph. Exemplary systems and methods are described in detail in U.S. Pat. No. 7,467,540 which is incorporated herein by reference in its entirety.

The system 10 can be used to perform similar analyses on gas condensate system samples. The separator gas and liquid samples can be physically recombined in system 10 in proportions defined by gas/oil ratio production data. This recombined reservoir fluid can then be used for subsequent analyses. The wellstream composition can be calculated based upon the measured compositions of the separator products and the gas/oil ratio.

A CCE test can be performed generally as described above with stepwise pressure reductions being performed at reservoir temperatures. The dewpoint (i.e., the pressure at which liquids begin to condense out the gas) rather than bubble point is identified.

Figure 9A:
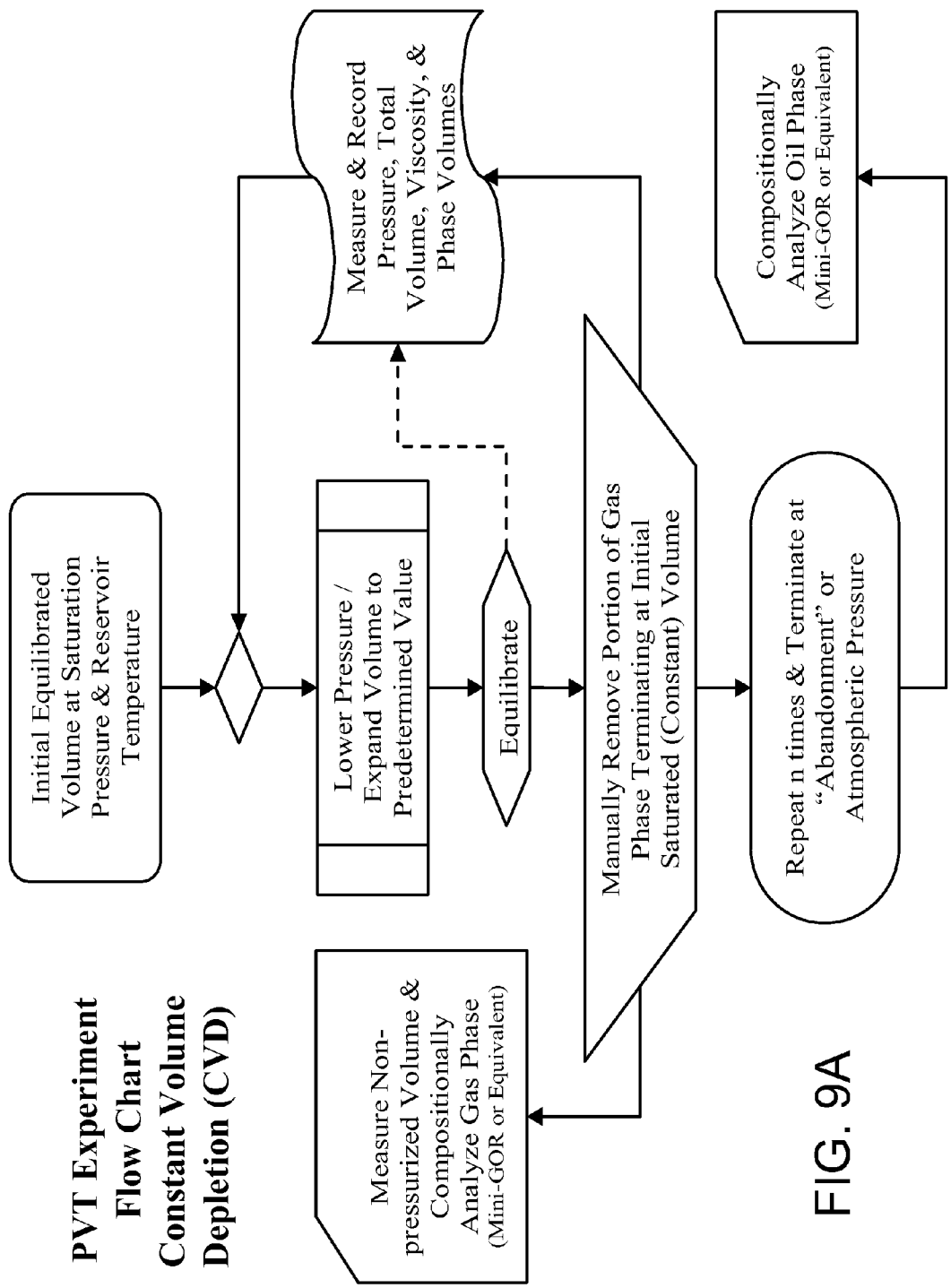
FIG. 9A is a flowchart of a constant volume depletion experiment.
Figure 9B:
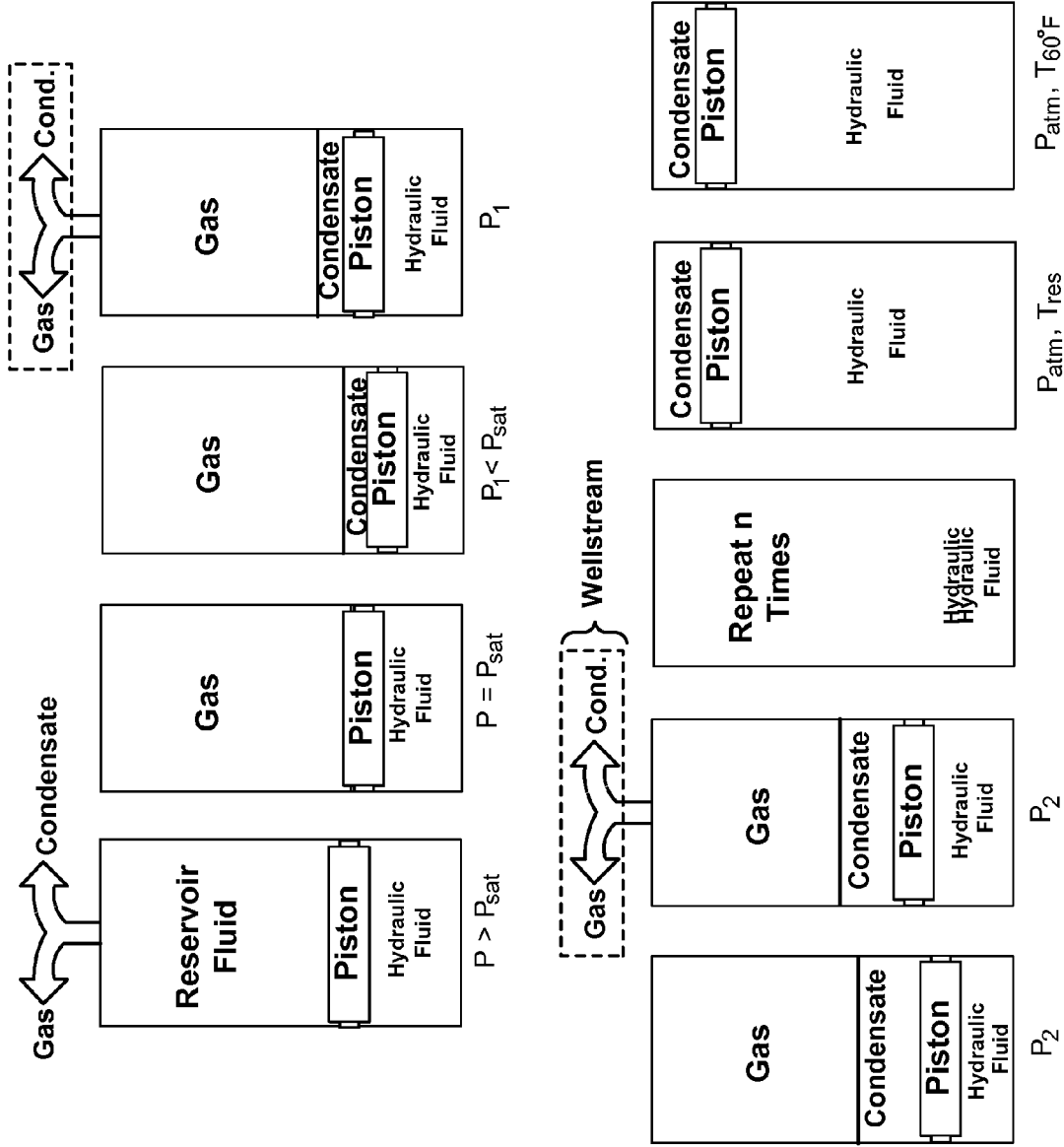
FIG. 9B is a schematic representation of a pressure cell during different stages of a constant volume depletion experiment.

Using the exemplary process illustrated in FIGS. 9A and 9B, a constant volume depletion (CVD) study can be performed in which system 10 is used to perform step-wise pressure drops between the observed dewpoint and anticipated abandonment pressure for the formation of interest. The operator provides the automated control system with input parameters including, for example, pressure increments. At each step, the sample can be mixed to equilibrate gas and liquid phases, the phase volumes measured, equilibrium gas phase removed (returning to saturated volume), liquid phase accumulation measured, and compositions of removed gas phases measured. These measurements allowed calculation of percent liquid dropout, percent produced, gas Z-factor, two-phase Z-factor, and hydrocarbon component concentrations all as functions of reservoir pressure depletion.

System 10 can also be used to perform various flow assurance measurements including, for example, identifying the wax appearance temperature, the asphaltene onset so pressure; and the flow rheology (shear dependency/viscosity of the system with gas in solution).

Figure 10:
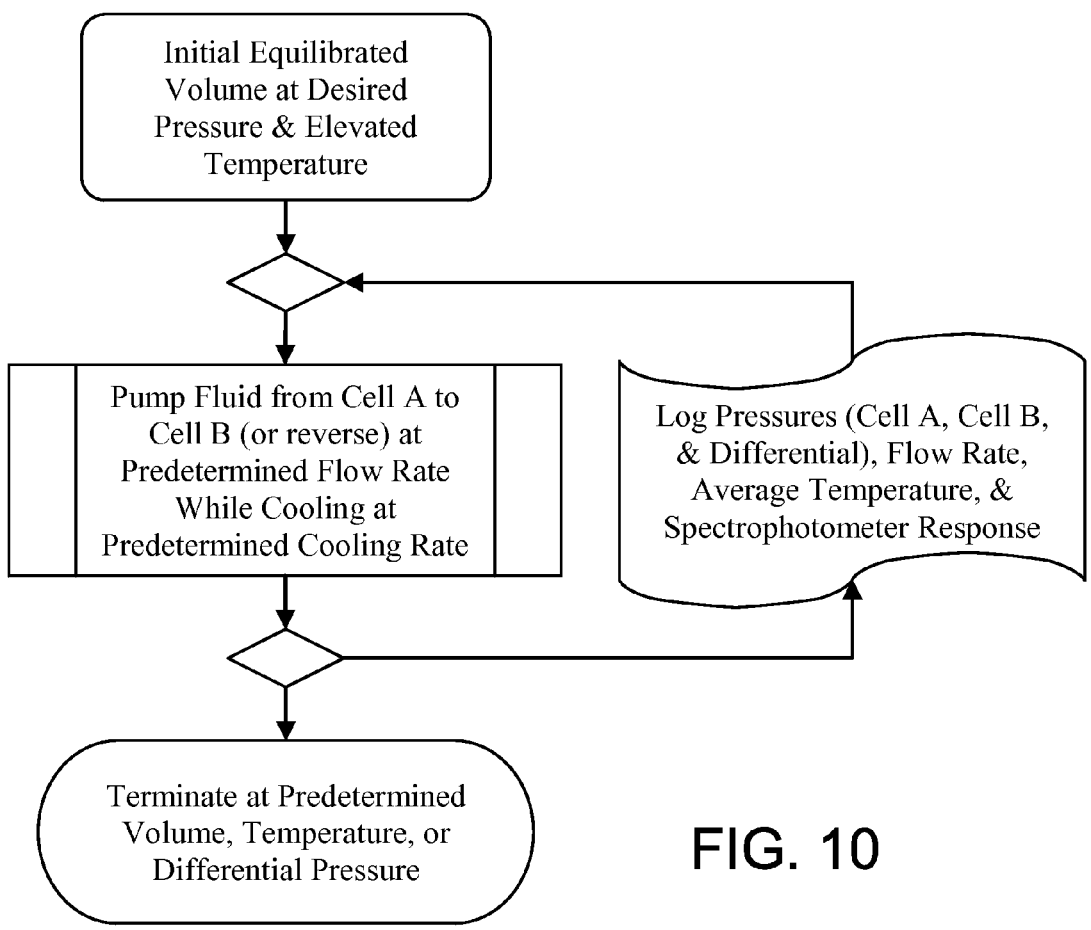
FIG. 10 is a flowchart of a wax appearance temperature experiment.

For example, it can be important to determine the temperature at which wax crystals form because such wax crystals can precipitate and plug production systems. System 10 is reconfigured for identifying the wax appearance temperature by replacing me capillary tube with a high-pressure filter. Using the exemplary process illustrated in FIG. 10, the wax appearance temperature can be identified. The operator provides the automated control system with input parameters including, for example, control pressure, cooling rate. The pistons 24 can be used to pump the sample fluid back and forth between the cells 12A, 12B while the environmental control chamber 14 gradually decreases the temperature being applied to the system from observed reservoir temperatures. As the wax appearance temperature is reached, wax crystals form and are captured by the filter such that the differential pressure measured by quartz gauges 20 goes up, and the light absorbance of the sample fluid as observed using the optics block 22 changes.

Figure 11:
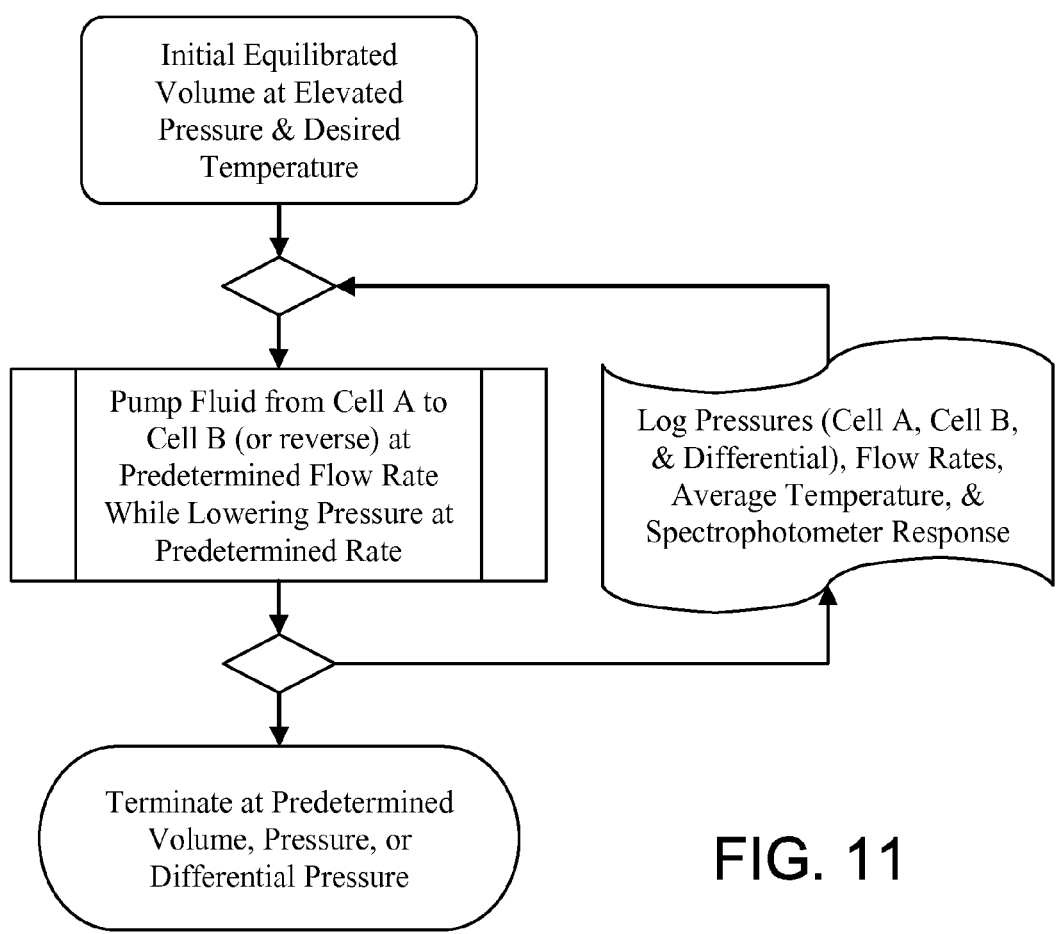
FIG. 11 is a flowchart of a asphaltene onset pressure experiment.

It can also be important to determine the pressure at which asphaltene begins to appear. Using the exemplary process illustrated in FIG. 11, the asphaltene appearance pressure can be identified. As with wax appearance temperature test, the system 10 is reconfigured by replacing the capillary tube with a high-pressure filter. The operator provides the automated control system with input parameters including, for example, controlled temperature and depressurization rate. The pistons 24 can be used to pump the sample fluid back and forth between the cells 12A, 12B while the pressure being applied to the sample fluid is gradually decreased from the observed reservoir pressure. As asphaltene forms, the differential pressure measured by quartz gauges 20 goes up and the light absorbance of the sample fluid as observed using the optics block 22 changes.

System 10 can also be used to perform Enhanced/Improved Oil Recovery Measurements with gases being considered for injection including, for example, assessing solubility/swelling, performing multiple gas contact forward & reverse) experiments, measuring viscosity changes with gas injection, and assessing revaporization.

For example, the solubility/swelling of reservoir fluids can be assessed by placing a sample in the cells 12A, 12B and injecting a given amount of a proposed injection gas into the system. After mixing the fluid to reach equilibrium conditions, the volume of the oil can be measured to determine how much the oil swells in response to the gas injection. A CCE test can be performed to test how the fluid bubble point changes in response to the gas injection. Changes in fluid viscosity in response to the gas injection can be measured using the capillary viscometer 18. These various changes can be measured as the function of the amount of gas injected into the system 10.

The system 10 can also be used to perform multiple gas contact (forward & reverse) experiments in which a specific volume of gas is injected into the system 10. Fluids in the system 10 can then be mixed until equilibrium conditions are achieved at a specific pressure. The remaining gas phase can then be removed from the system to assess liquid phase swelling, shrinkage, and gas phase enrichment. The steps can then be repeated with a fresh injection gas. Alternatively, rather than removing the remaining gas phase, the liquid phase will be removed from the system 10 to assess liquid phase swelling and enrichment from the injected gas.

System 10 can also be used to test chemical products such as, for example, inhibitors, dispersants, anti-drag products, and de-emulsifiers. The general tests described above can be performed after injecting a specific chemical product into the system 10 to assess the likely effects of the specific chemical product on fluid in the reservoir from which the sample being tested was taken.

System 10 can also be used to measure the properties such as, for example, fluid compressibility, thermal expansion, gas solubility, and viscosity as functions of pressure and temperature.

Although not necessary for the concepts described herein, combining and automating operations can eliminate the additional equipment used in performing PVT experiments of the sample. In many cases, the additional equipment required to analyze the liquid phase is voluminous and cannot be maintained in small lab facilities. The equipment is also not feasibly transported. As a result, the equipment necessary to perform PVT experiments, as well as the remainder of the equipment needed to analyze the sample, are maintained in centralized testing facilities in various locations about the world. A sample may travel tens or hundreds of miles from the location at which it is taken to the centralized testing facility.

For example, although offshore platforms typically maintain a small lab, the space on the platform does not allow the equipment necessary to perform PVT experiments. Therefore, a sample taken on the offshore platform would normally be transported to an onshore testing facility. Similarly, it is not practical to maintain the voluminous analysis equipment at remote onshore sampling sites, such as sites in rural areas. Depending on the location of the offshore platform or rural onshore sampling site, the sample may travel tens or hundreds of miles to reach the testing facility. This travel introduces a many hour lag between the time the sample is taken and the time the analysis can be performed. This time lag discourages frequent testing and hinders retesting. The travel increases the is likelihood that the sample will become compromised and or contaminated, and introduces additional expenses in travel and time into the costs of analysis. If a sample is contaminated or fouled, during collection, transport or otherwise. It will not be discovered until the sample has traveled the many miles to reach the centralized testing facility. Another sample must then be taken and transported to the centralized testing facility or the analysis forgone.

Figure 12:
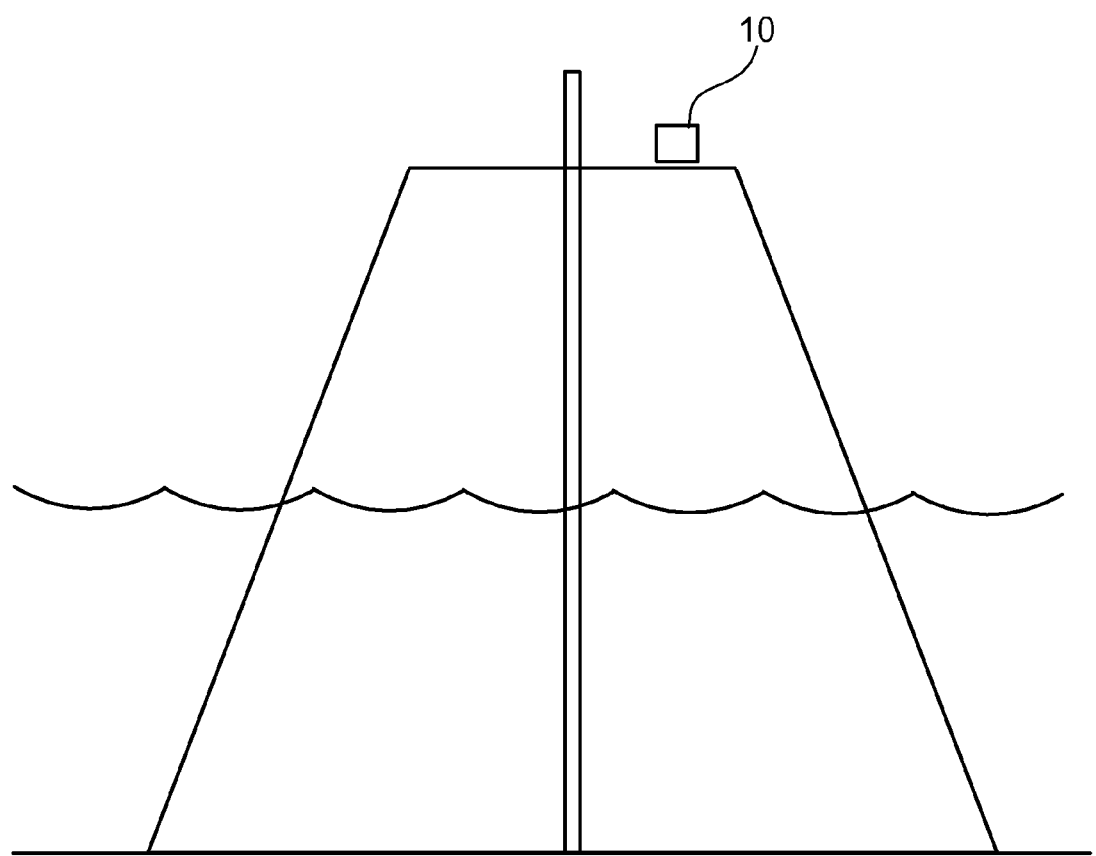
FIG. 12 is a schematic illustration of an analysis system deployed to a drilling platform.

In contrast, testing systems as illustrated by system 10 described above can be smaller, easily transported and can be maintained in a small lab facility. Thus, the analysis system 10 can be maintained at or near the sampling location. For example, as illustrated in FIG. 12, the analysis system 10 can be maintained on an offshore platform. Maintaining the analysis equipment at the sampling location enables frequent testing and eliminates the time delay and costs associated with transporting the sample. If it is not feasible to maintain the entire analysis equipment at the sampling location, the analysis equipment can be transported to the sampling location. Having the analysis equipment near the sampling location enables quick retesting if the sample is contaminated during collection, transport or otherwise.

A number of embodiments of the invention have been described. Nevertheless, it will be understood that various modifications may be made without departing from the spirit and scope of the invention. Accordingly, other embodiments are within the scope of the following claims.

What is claimed is:

1. A pressure-volume-temperature (PVT) testing system comprising:
    a portable environmental control chamber;
    a first pressure vessel disposed inside the portable environmental control chamber;
    a second pressure vessel disposed inside the portable environmental control chamber, the second pressure vessel in hydraulic communication with the first pressure vessel;
    a viscometer configured to measure the viscosity of fluid flowing between the first pressure vessel and the second pressure vessel; and
    an optics system configured to measure optical properties of the fluid flowing between the first pressure vessel and the second pressure vessel;
    wherein the pressure vessels are rotatable within the portable environmental control chamber to control vertical positions of the first and second pressure vessels relative to conduits connecting the first pressure vessel to the second pressure vessel.

2. The testing system of claim 1, wherein the viscometer comprises a capillary viscometer located such that the fluid flowing between the first pressure vessel and the second pressure vessel flows through the capillary viscometer.

3. The testing system of claim 2, wherein the viscometer comprises two quartz gauges operable to measure temperature and pressure of fluid, a first quartz gauge on one side of capillary tubing and a second quartz gauge on another side of the capillary tubing.

4. The testing system of claim 1, wherein the optics system comprises a spectrophotometer optically coupled to an optics bock with fiber optic cables, the optics block located such that the fluid flowing between the first pressure vessel and the second pressure vessel flows through the optics block.

5. The testing system of claim 1, further comprising an automated control system operable to determine specific hydrocarbon phase volumes based at least in part on data from the optics system.

6. The testing system of claim 1, wherein the first and second pressure vessels comprise pistons separating sample fluid from hydraulic fluid.

7. The testing system of claim 1, further comprising an automated control system operable to electronically communicate with the viscometer, with the optics system, and with pumps in hydraulic communication with first and second pressure vessels.

8. The testing system of claim 7, wherein the automated control system is operable to control the pumps during PVT experiments including: Constant composition expansion (CCE), Differential liberation (DLE), Constant volume depletion (CVD), Separator test(s), Viscosity measurements, Wax appearance temperature (WAT), and Asphaltene onset experiments based on data from the pumps, optics system, and viscometer without requiring operator input beyond inputting initial experiment parameters.

9. The testing system of claim 8, wherein the automated control system is operable to perform more than one of the experiments concurrently.

10. The testing system of claim 1, wherein the portable environmental control chamber comprises a control chamber operable to control the temperature of fluid in the pressure vessels.

11. The testing system of claim 10, wherein the environmental control chamber is operable to provide temperatures ranging from 0° to 350° F. and to allow isothermal and programmed ramp temperature control.

12. The testing system of claim 1, wherein the first and second pressure vessels and associated fittings and connections are configured to contain pressures of up to 20,000 psia.

13. The testing system of claim 1, configured to provide pressure, temperature, and volumetric accuracy and control to within 2% overall.

14. The testing system of claim 6 wherein the first pressure vessel comprises a cone-shaped head assembly and the piston separating sample fluid from hydraulic fluid in the first pressure vessel is coned to a similar angle as the cone-shaped head assembly.

15. The testing system of claim 1, wherein the first pressure vessel and the second pressure vessel are pivotably mounted such that the first pressure vessel and the second pressure vessel can be rotated to and fixed in multiple orientations relative to the environmental control chamber.

16. The testing system of claim 15, wherein, in a first orientation relative to the environmental control chamber, the first and second pressure vessels are located above inlets to tubing providing hydraulic connection between the first and second pressure vessels and, in a second orientation relative to the environmental control chamber, the first and second pressure vessels are located below the inlets to the tubing providing hydraulic connection between the first and second pressure vessels.

17. A method of testing fluids, the method comprising:
    with a testing system residing at a site where a sample fluid is withdrawn from a subterranean formation;
    controlling temperature and pressure of the sample fluid in the testing system;
    equilibrating the sample fluid by transferring the sample fluid between a first pressure vessel and a second pressure vessel in hydraulic communication with the first pressure vessel;
    controlling vertical positions of the first pressure vessel and the second pressure vessel relative to conduits connecting the first pressure vessel to the second pressure vessel;

measuring viscosity of fluid flowing between the first pressure vessel and the second pressure vessel while equilibrating the sample fluid; and measuring optical properties of the fluid flowing between the first pressure vessel and the second pressure vessel while equilibrating the sample fluid.

18. The method of claim 17, wherein controlling the temperature of the sample fluid comprises controlling the temperature of the sample fluid using a portable environmental control chamber containing the first and second pressure vessels.

19. The method of claim 17, further comprising adjustably controlling orientation of the first and second pressure vessels within the portable environmental control chamber.

20. The method of claim 18, further comprising using the portable environmental control chamber to decrease the temperature of the sample fluid at a specified rate.

21. The method of claim 17, further comprising identifying phase change boundaries in the sample fluid based on changes in the optical properties of portions of the sample fluid.

22. The method of claim 17, comprising performing at least two of a constant composition expansion test, a differential liberation test, viscosity, a constant volume depletion test, a separation test, a wax appearance temperature test, and an asphaltene onset test concurrently on fluid in the first and second pressure vessels.

23. The method of claim 17, comprising controlling the vertical orientation of the first and second pressure vessels to sub-sampling, analysis, or both of a specific hydrocarbon phase.

24. A pressure-volume-temperature testing system comprising:
   a portable environmental control chamber;
   a first pressure vessel disposed inside the portable environmental control chamber; and
   a second pressure vessel disposed inside the portable environmental control chamber, the second pressure vessel in hydraulic communication with the first pressure vessel;

wherein the portable environmental control chamber is operable to controllably heat and cool fluid in the first and second pressure vessels; and wherein the pressure vessels are rotatable within the portable environmental control chamber to control vertical positions of the first and second pressure vessels relative to conduits connecting the first pressure vessel to the second pressure vessel.

25. The testing system of claim 24, further comprising a viscometer configured to measure the viscosity of fluid flowing between the first pressure vessel and the second pressure vessel wherein the viscometer is a capillary viscometer located such that the fluid flowing between the first pressure vessel and the second pressure vessel flows through the capillary viscometer.

26. The testing system of claim 24, further comprising an optics system configured to measure optical properties of the fluid flowing between the first pressure vessel and the second pressure vessel.

27. The testing system of claim 24, further comprising a spectrophotometer optically coupled to an optics bock with fiber optic cables, the optics block located such that the fluid flowing between the first pressure vessel and the second pressure vessel flows through the optics block.

28. The testing system of claim 27, further comprising a programmable control module operable to electronically communicate with the viscometer, with the optics system, and with pumps in hydraulic communication with first and second pressure vessels.

29. The testing system of claim 28, wherein the programmable control module is operable to perform at least two of a constant composition expansion test, a differential liberation test, viscosity, a constant volume depletion test, a separation test, a wax appearance temperature test, and an asphaltene onset test simultaneously on fluid in the first and second pressure vessels.

* * * * *